US011801017B2

(12) United States Patent
Olson et al.

(10) Patent No.: US 11,801,017 B2
(45) Date of Patent: Oct. 31, 2023

(54) FOCUSED TOMOGRAPHY

(71) Applicant: University of Florida Research Foundation, Inc., Gainesville, FL (US)

(72) Inventors: Timothy Edward Olson, Deland, FL (US); Stephanie Marie Leon, Newberry, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/986,014

(22) Filed: Aug. 5, 2020

(65) Prior Publication Data

US 2021/0038172 A1 Feb. 11, 2021

Related U.S. Application Data

(60) Provisional application No. 62/884,230, filed on Aug. 8, 2019.

(51) Int. Cl.
*A61B 6/00* (2006.01)
*A61B 6/03* (2006.01)
*G01N 23/046* (2018.01)
*A61B 6/06* (2006.01)

(52) U.S. Cl.
CPC ............... *A61B 6/032* (2013.01); *A61B 6/03* (2013.01); *A61B 6/06* (2013.01); *A61B 6/405* (2013.01); *A61B 6/4028* (2013.01); *G01N 23/046* (2013.01); *G01N 2223/419* (2013.01)

(58) Field of Classification Search
CPC ......... A61B 6/03; A61B 6/4028; A61B 6/405; A61B 6/06; G01N 23/046; G01N 2223/419; G01N 2223/316
See application file for complete search history.

(56) References Cited

U.S. PATENT DOCUMENTS

| 10,628,974 | B2 * | 4/2020 | Cao ........................ G06T 11/006 |
| 2004/0264626 | A1 * | 12/2004 | Besson ................... A61B 6/563 |
| | | | 378/4 |
| 2009/0202035 | A1 * | 8/2009 | Tsukagoshi ............ A61B 6/481 |
| | | | 378/8 |
| 2010/0091937 | A1 * | 4/2010 | Raupach .............. A61B 6/4035 |
| | | | 378/16 |

(Continued)

Primary Examiner — David P Porta
Assistant Examiner — Mamadou Faye
(74) Attorney, Agent, or Firm — Thomas | Horstemeyer, LLP

(57) ABSTRACT

An exemplary focused tomography system comprises an x-ray transmitter that is configured to emit a radiation beam and an x-ray detector that is configured to detect incident radiation from the radiation beam. The system further includes an adaptive collimator device arranged between the x-ray transmitter and the x-ray detector and a controller device connected to the x-ray transmitter that is configured to cause the x-ray transmitter to emit the radiation beam at a first radiation dosage level when a path of the radiation beam intersects a region of interest of the subject and cause the x-ray transmitter to emit the radiation beam at a second radiation dosage level when the path of the radiation beam does not intersect the region of interest of the subject, such that the second radiation dosage level is less than the first radiation dosage level. Data within the region of interest can be reconstructed with image quality equivalent to traditional computed tomography scans.

19 Claims, 29 Drawing Sheets

(56) References Cited

U.S. PATENT DOCUMENTS

| | | | |
|---|---|---|---|
| 2010/0119033 A1* | 5/2010 | Li | A61B 6/06 378/5 |
| 2010/0246756 A1* | 9/2010 | Forthmann | G21K 1/10 378/16 |
| 2012/0099697 A1* | 4/2012 | Helm | A61B 6/542 378/4 |
| 2012/0140874 A1* | 6/2012 | Li | A61B 6/032 378/11 |
| 2013/0272504 A1* | 10/2013 | Deutsch | G21K 1/04 378/150 |
| 2018/0228452 A1* | 8/2018 | Badal-Soler | A61B 6/544 |

* cited by examiner

FOCUSED TOMOGRAPHY

CROSS-REFERENCE TO RELATED APPLICATION

This application claims priority to U.S. provisional application entitled, "Focused Tomography," having Ser. No. 62/884,230, filed Aug. 8, 2019, which is entirely incorporated herein by reference.

BACKGROUND

The National Institutes of Health (NIH) has noted that computerized tomography (CT) use is up over 2000% in the last 20 years. In the 1990's, CT machines were primarily used for post-diagnostic tests. They are now often used for pre-diagnostic tests especially in the case of trauma such as car accidents, etc. Accordingly, CT use has become so prevalent that the cumulative radiation dosage which patients are exposed to during their lifetime has increased dramatically. This long term exposure risks cancerous outcomes as a result of the CT scans. Thus, the cost-benefit analysis arises: (1) one or more CT exam vs. (2) the possibility of long term health complications. X-ray radiation is generally considered carcinogenic, or cancer creating. The goal of this project is to allow the positive use of CT, while minimizing the amount of radiation used.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 8A-8B are diagrams comparing image reconstructions from local data, in which FIG. 8A illustrates localized reconstruction in accordance with embodiments of the present disclosure and FIG. 8B illustrates an image reconstruction from totally local data.

DETAILED DESCRIPTION

The present disclosure describes systems and methods for improving the focusing of computerized tomography (CT) machines, such as all of those currently in use. This will allow one to image portions of the human anatomy, such as the spine, shoulders, hips, and elbows, without exposing an entire slice of the human body to a full radiation (x-ray) dose.

Computerized tomography (CT) has become a standard diagnostic tool in modern medicine. In the last 30 years, however, CT use has become so prevalent that the cumulative radiation dosage which patients are exposed to during their lifetime has increased dramatically. The risk/reward tradeoffs for these diagnostic tools are hard to quantify. Often times a physician is only interested in a limited region of interest (ROI) which has been identified through clinical means or previous imaging. We believe that the risk can be reduced when a limited ROI is of interest by significantly reducing the total radiation dosage. The reward of this imaging will be preserved, since the images of the ROI will be nearly identical to those achieved with full radiation dosage. Large radiation dosages are well known to be potential causes for cancer.

Figure 2:
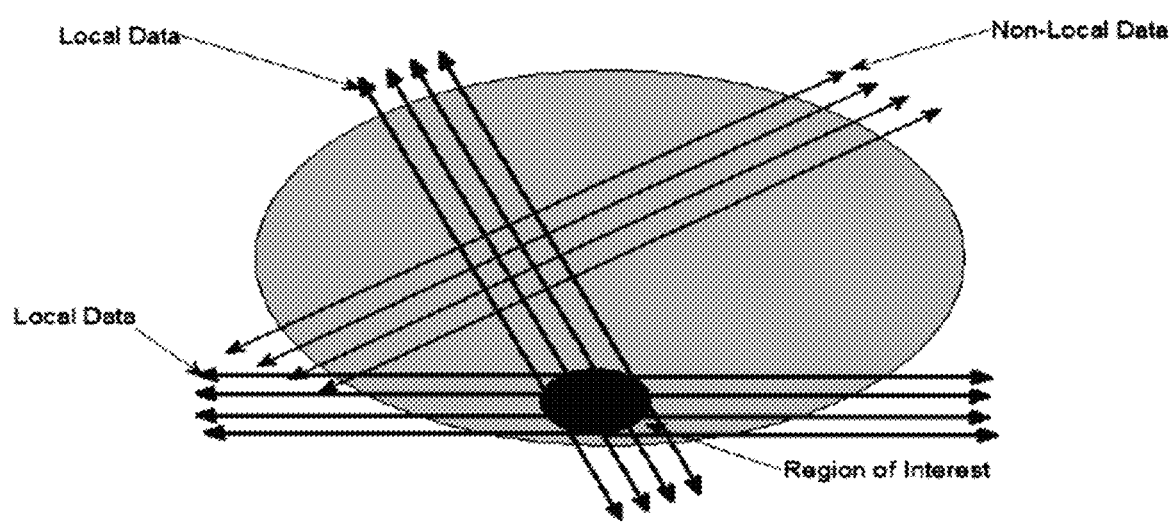
FIG. 2 is a diagram depicting a region of interest, local data, and non-local data in accordance with embodiments of the present disclosure.

The original investigations into region of interest (ROI) tomography, called local tomography, did not return the actual density of the ROI. Rather these returned an altered or transformed image which did preserve edges between varying tissues. The goal of local tomography is returning the actual image of the ROI. This is possible when one realizes that the low frequency components of the image are the only components which need non-local x-rays for their estimation. The high frequency components can be measured with the local line integral measurements which pass through the ROI. Thus, one does not need to send high dosage radiation on paths which do not intersect the ROI to find the high frequency components of the image. In FIG. 2, an illustration of local versus non-local x-ray paths is depicted. Low radiation measurements may then be used to measure the non-local information.

In the figure of FIG. 2, concepts are depicted for a region of interest (ROI), local data, and non-local data. The region of interest (ROI), is the dark portion, which might be an approximation for the spinal column of a patient. A portion of the lines represents x-ray paths which pass through the ROI, and are therefore called local x-ray paths. The other lines represent x-ray paths that do not intersect the ROI, and are therefore referred to as non-local x-ray paths. The systems and methods of the present disclosure will minimize radiation along non-local x-ray paths.

Thus, to provide a complete and accurate reconstruction of the ROI, two earlier methods feature (a) regular sampling of the x-rays through the ROI in order to reconstruct the high frequency components of the image via a computer processor of the CT scanner, and (b) sparse sampling of the x-rays which do not intersect the ROI, allowing for the recovery of low frequency components of the image. The combination of these methods results in an accurate reconstruction of the ROI with greatly reduced radiation dosages. These earlier methods work very well but only allow 0-1 sampling, i.e. either an x-ray is measured along a line integral or it is not. This is not feasible with current computerized tomography mechanisms.

The present disclosure concentrates on new improved methods and systems, which allow for variable sampling of the x-rays by featuring regular dosage radiation through the ROI & dramatically reduced dosage radiation through the portions of the body outside of the ROI. The lower dosage measurements outside of the ROI will be sufficient because they will only be utilized to determine the low-frequency components of the ROI image.

Thus, the lower signal to noise ratio (SNR) measurements (at lower radiation dosages) can be averaged producing adequate SNR measurements for these low frequency components. The detailed high-frequency components of the image will have standard SNR measurements (at standard radiation dosages). Thus, the image in the ROI can be made arbitrarily close to that using complete radiation dosage, with dramatically lower dosages.

Various systems and methods of the present disclosure will allow physicians to view and monitor regions of interest using radiation dosages outside the ROI which are 10% or less of the standard dosage. This work will augment, rather than compete with, efforts which primarily focus on improving receiver sensitivity.

Figure 3A:
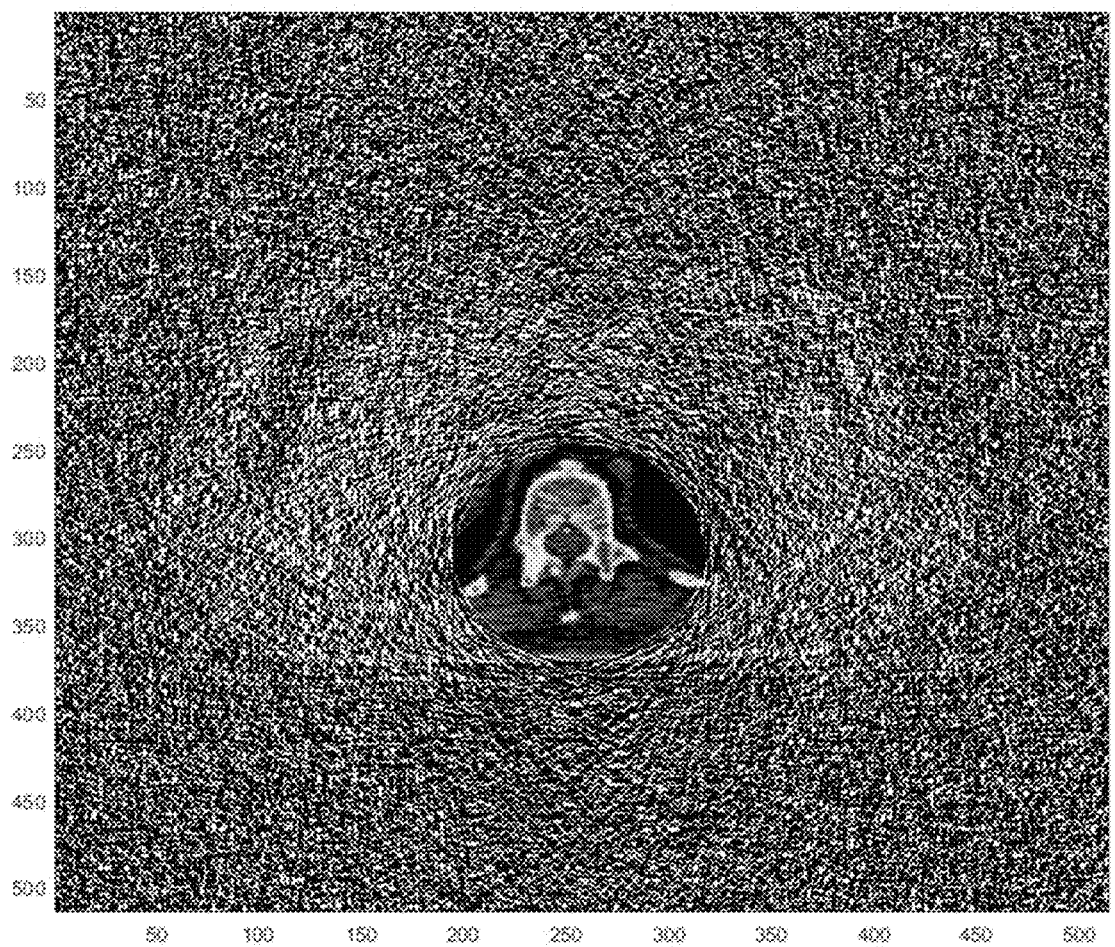
FIGS. 3A-3B show focused tomography images on a portion of a subject's spine and hip in accordance with embodiments of the present disclosure.
Figure 3B:
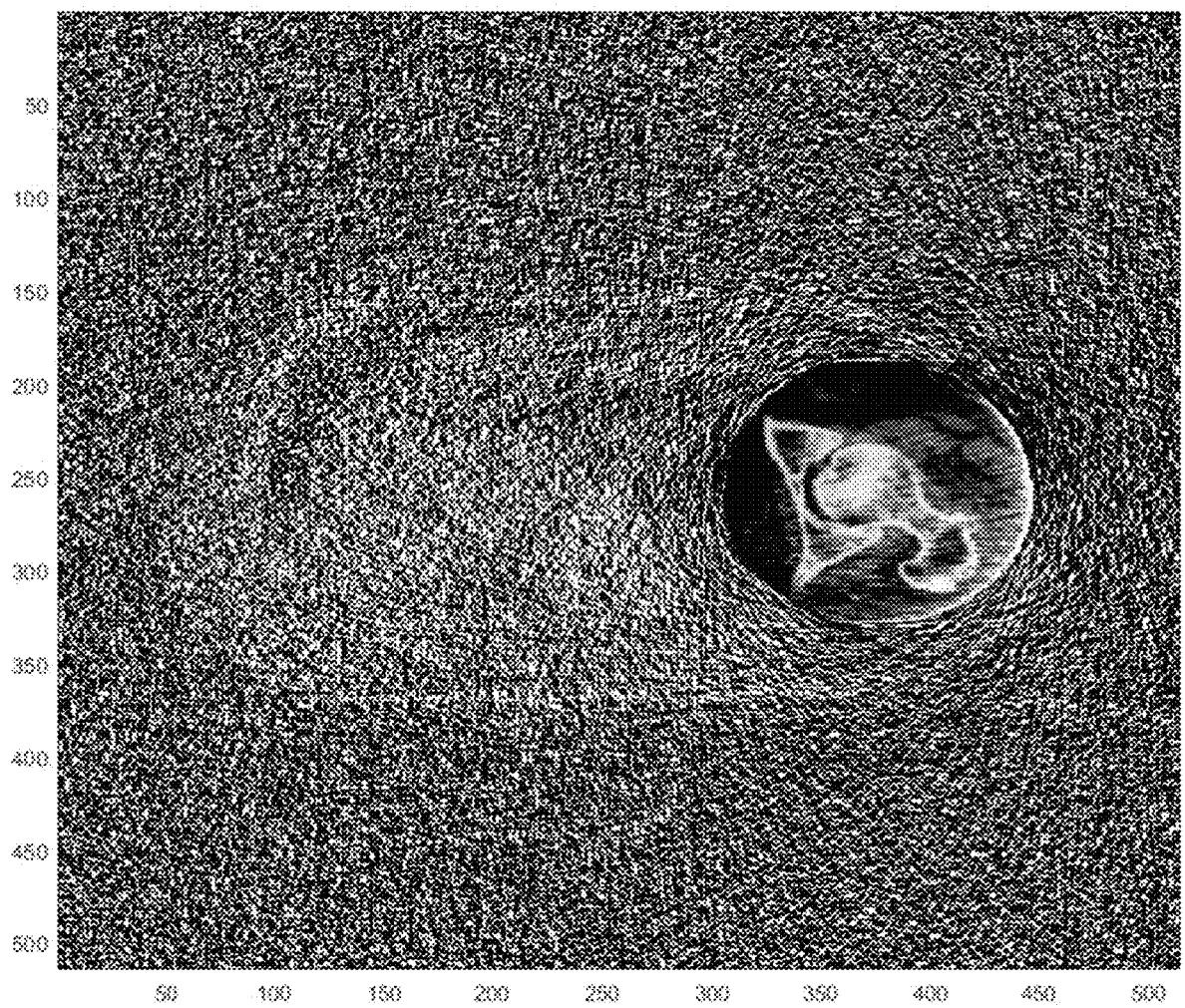

Current clinical practice is to choose a body segment to be imaged, and expose the entire portion to the same radiation levels. Thus, if the right shoulder is the region of interest, the entire chest from the neck to below the shoulder will be exposed to the same amount of radiation. In accordance with teachings of the present disclosure, physicians will be enabled to ask for only an image of the right shoulder or ROI. Accordingly, systems and methods of the present disclosure may then concentrate radiation on that ROI and use a greatly reduced amount of radiation on the rest of the upper chest cavity and neck. Similarly, when doing spinal imaging, the radiation will be concentrated on that portion of the spine which is of interest, minimizing the radiation elsewhere, as demonstrated by FIG. 3A showing focused tomography on a portion of a subject's spine in accordance with embodiments of the present disclosure. This development will constitute a shift in clinical practice, which can eliminate up to 80% of the total radiation dosage.

This focused tomography may be especially meaningful concerning diagnostic endeavors with children and pregnant women. The present disclosure discusses the imaging of tissue structures in cylindrical volumes (while also contemplating the use of non-cylindrical volumes). The mathematical methods of the present disclosure promise the possibility of imaging within formed structures that can directly follow the outline of the anatomy under concern. There are many organs in the human body which are well known to be susceptible to radiation exposure. Minimizing risk to these organs is one focus of the present disclosure.

Figure 1:
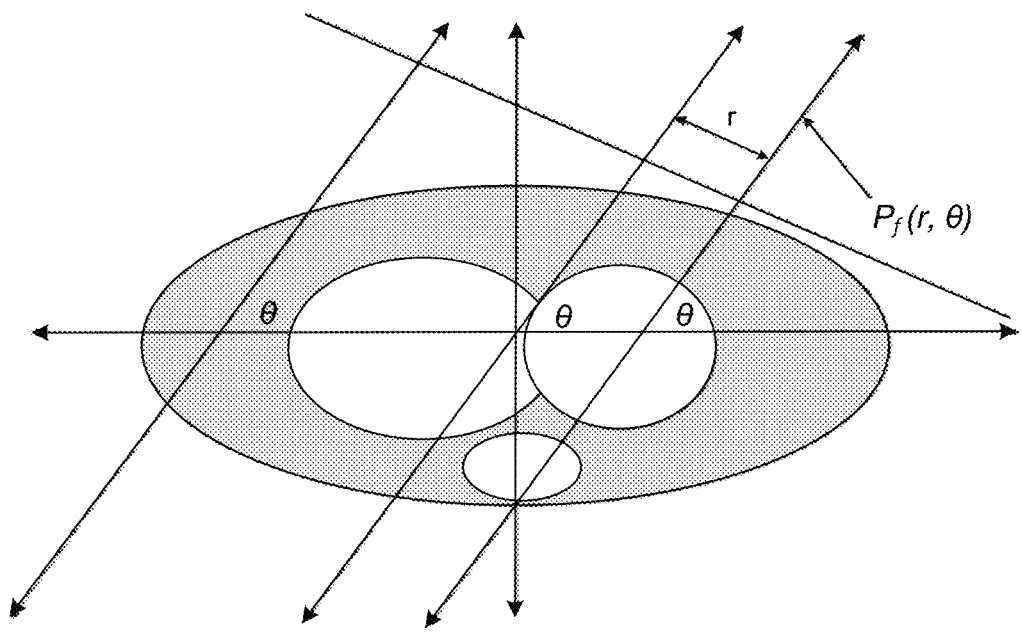
FIG. 1 is a diagram illustrating the basics of projection angles, coordinates, and vectors, r, $\theta$, $\vec{\theta}$, and $\vec{x}$, in accordance with the present disclosure.

This focused tomography can be accomplished through a thorough understanding of the CT reconstruction process. CT data is generally collected in a helical fan-beam geometry. For the discussion of the reconstruction process, it is easier if we assume that this data has been reformatted into a parallel beam data set. Thus, the present disclosure assumes that the data can be viewed as a function of two variables, angle $\vec{\theta}$ and distance r from the origin, or that the data, which is referred to as the projections or sinogram, has the form $$P_f(r, \vec{\theta}) = \int f(r\vec{\theta} + t\vec{\theta}^{\perp}) dt \qquad (1)$$

where t is an arbitrary variable chosen for the purposes of integration. The basics of the CT projection is illustrated in FIG. 1.

To this end, let us recall that the natural coordinates for tomography are $x = r\vec{\theta} + t\vec{\theta}^{\perp} = r$. Moreover, $\vec{x} \cdot \vec{\theta}^{\perp} = r$. We want to see what the Fourier coefficients propagating at a fixed direction $\vec{\theta}$ have in common with the projections, so the present disclosure considers $$\hat{f}(s\vec{\theta}) = \frac{1}{2\pi} \int P_t(r, \vec{\theta}) e^{irs} dr. \qquad (2)$$

where s is radial polar component of the polar representation of the Fourier transform. Thus, a central slice of the two dimensional Fourier transform of f (x, y), i.e. $\hat{f}(s\vec{\theta})$ can be obtained from the one dimensional projections of the function or $P_f(r, \vec{\theta})$. Formally stated, we have Theorem 2.1 (Radon Transform, or Central Slice Theorem), as described below.

Theorem 2.1.

The one dimensional Fourier transform of $P_f(\vec{\theta}, r)$ is given by the central slice of the two dimensional Fourier transform, or $\hat{f}(s\vec{\theta})$. Mathematically, $$\mathcal{F}_1(P_f(r, \vec{\theta})) = \frac{1}{\sqrt{2\pi}} \hat{f}(s\vec{\theta}). \qquad (3)$$

From this formula one can quickly derive the Filtered Backprojection formula, which was the basis of the 1979 Nobel Prize.

$$f(\vec{x}) \approx \frac{1}{2\pi} \int_0^\pi \int_{-\infty}^\infty \hat{f}(s\vec{\theta})|s|w(s)e^{irs} ds d\theta \qquad (4)$$

$$= \int_0^\pi (P_f(r, \theta) * \mathcal{F}^{-1}(|s|w(s)))(\vec{x} \cdot \vec{\theta}) d\theta,$$

where |w(s)| is the frequency cut-off window.

By choosing w(s) appropriately, we can make the approximation above arbitrarily small. If we denote $\mathcal{F}^{-1}(|s|w(s)) = k(r)$ then, by the convolution theorem, we have $$f(\vec{x}) \approx \int_0^\pi (P_f(r, \theta) * k(r))(\vec{x} \cdot \vec{\theta}) d\theta, \qquad (5)$$

where * denotes convolution.

One problem with Equation (5) is that the kernel k(r) is very broad as a function of r, and as a result, radiation measurements must be taken far from the region of interest. The reason for this kernel being broad is the jump discontinuity of the derivative of the function |s| at the origin from −1 to 1. Recall that |s| is the necessary term due to the polar coordinates used in the Fourier inversion of the filtered backprojection formula (4). The basic theorems of Fourier analysis dictate that this kernel cannot decay quickly.

Figure 4:
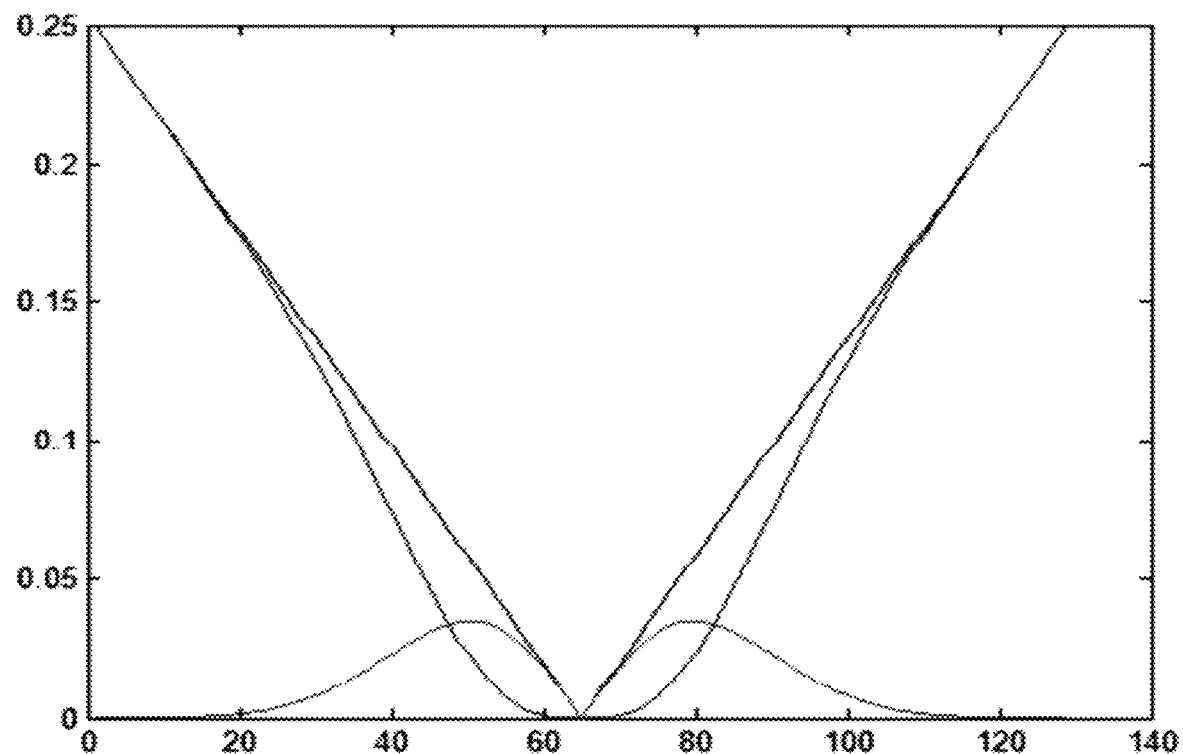
FIG. 4 is a diagram showing the correction term necessary for the inverse Fourier transform in polar coordinates in accordance with embodiments of the present disclosure.

This problem is solved by separating the discontinuity at the origin of |s| into separate portions: $|s|w_2(s)$ at the origin and $|s|(1-w_2(s))$ away from the origin, as illustrated in FIG. 4. The corresponding inverse Fourier transforms will be a low frequency kernel $k_l(r)$ which is the inverse Fourier transform of $|s|w_2(s)$, and a low frequency kernel $k_h(r)$ which is the inverse Fourier transform of $|s|(1-w_2(s))$.

Referring back to FIG. 4, the figure shows the correction term necessary for the inverse Fourier transform in polar coordinates above, i.e. |s|. The problem with |s| is the jump discontinuity at the origin of the derivative of |s|, from 1 to negative 1. This dictates that the inverse Fourier transform of $|s|w(s)$, even with a suitably smooth window w(s), will be very wide, rather than narrow. This can be solved as above, with one "low frequency" term at the origin and a "high frequency" term. The corresponding decomposition of the kernel $k(r) = k_l(r) + k_h(r)$ will result in a low frequency kernel as a function of radius, $k_l(r)$, which is not locally supported, and a high frequency kernel $k_h(r)$ which is very narrow as a function of radius.

Figure 5:
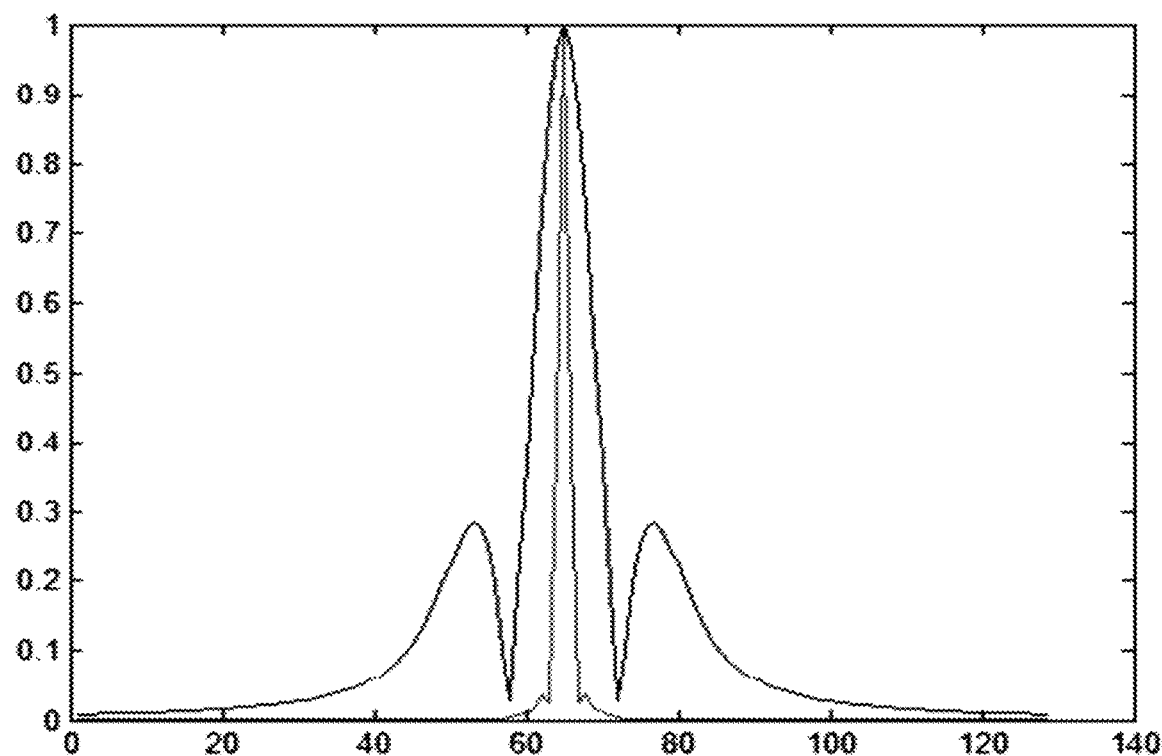
FIG. 5 is a diagram showing kernel decompositions $k_l(r)$ and $k_h(r)$ in accordance with embodiments of the present disclosure.

Thus, we have $k(r) = k_l(r) + k_h(r)$. The filtered backprojection algorithm now looks like $$f(\vec{x}) \approx \int_0^\pi (P_f(r, \theta) * k(r))(\vec{x} \cdot \vec{\theta}) d\theta$$

$$= \int_0^\pi (P_f(r, \theta) * k_l(r))(\vec{x} \cdot \vec{\theta}) d\theta + \int_0^\pi (P_f(r, \theta) * k_h(r))(\vec{x} \cdot \vec{\theta}) d\theta, \qquad (6)$$

$$= f_l(\vec{x}) + f_h(\vec{x}), \qquad (7)$$

and, we will reconstruct, via a computer processor, the low and high frequency terms of $f(\vec{x})$ separately. The kernels are illustrated in FIG. 5 which shows the kernel decompositions $k_l(r)$ and $k_h(r)$.

The energy of $k_h(t)$ is contained within the interior 9 pixels of the current digitization or 9/512 to an accuracy of 1/10000. The energy concentration of $k_l(r)$, similarly measured, takes 175 terms. The low frequency terms take a great deal of non-local information, and the high frequency terms can be measured locally.

Initially, there seems to be no advantage to the change to two kernels $k_l(r)$ and $k_h(r)$ from a radiation reduction standpoint. The low frequency kernel will require the gathering of large quantities of data from outside the region of interest. Thus, there is no apparent win in the fact that the high frequency component $f_h(\vec{x})$ can be calculated from completely local measurements. One must understand the structure of the projections, and corresponding structure of the filtered backprojection algorithms to see how to solve the problems with the low frequency reconstruction $f_l(\vec{x})$. The structure theorem for the projections or Radon transform states that $$P_f(\vec{\theta}, r) = (1 - r^2)^{-1/2} \sum_{l=0}^{\infty} T_l(r) h_l(\theta), \quad (8)$$

where $T_l(r)$ are the Chebyshev polynomials. Taking the Fourier transform of this yields $$\hat{f}(s\vec{\theta}) = \hat{P}_f(\theta, s) = \left(\frac{\pi}{2}\right)^{-\frac{1}{2}} \sum_{l=0}^{\infty} i^{-1} J_l(s) h_l(\theta) \quad (9)$$

$$= \left(\frac{\pi}{2}\right)^{-1/2} \sum_{l=0}^{N-1} i^{-1} J_l(s) h_l(\theta) + \left(\frac{\pi}{2}\right)^{-\frac{1}{2}} \sum_{l=N}^{\infty} i^{-1} J_l(s) h_l(\theta) \quad (10)$$

$$= \hat{f}_l(s, \theta) + \hat{f}_h(s, \theta) \quad (11)$$

where $J_l(s)$ are the Bessel functions, and $h_l(\theta)$ is a trigonometric polynomial of order 1. The key to understanding Equation (9) is that the low frequency terms in s, which are the Bessel functions, are only multiplied in frequency by the low order terms $h_l(\theta)$. Thus, the low frequency terms do not have to be measured for many angles θ in order to accurately determine the complete low frequency components of the image.

Figure 6A:
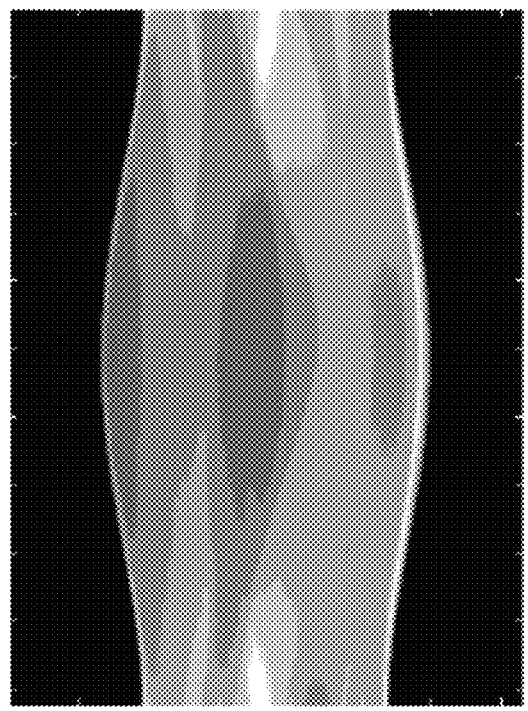
FIGS. 6A-6B are diagrams illustrating a standard Radon transform and sampling schemes.
Figure 6B:
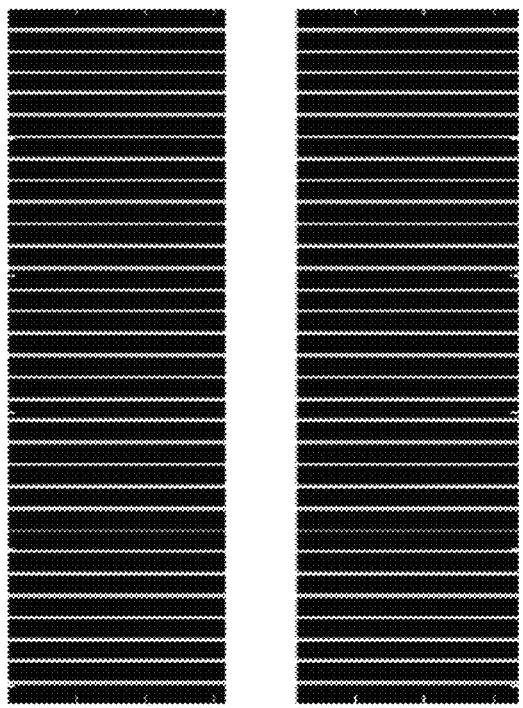
Figure 6C:
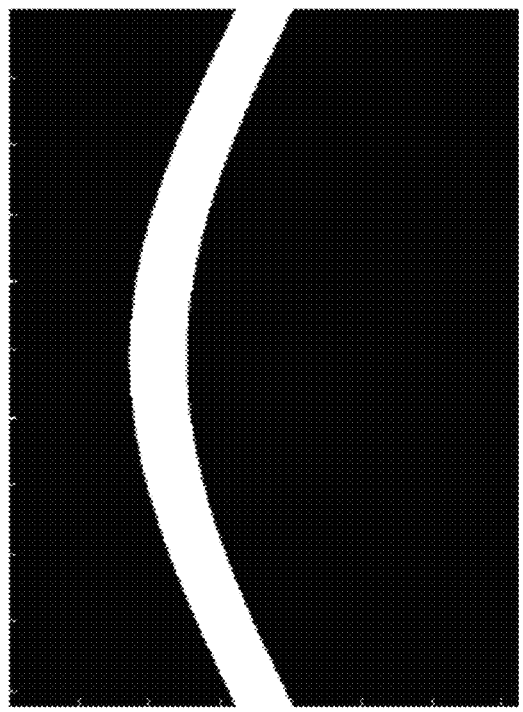
FIG. 6C shows the sampling scheme in accordance with embodiments of the present disclosure. High frequency on the central portion, and low frequency off the central portion.

The sampling of the projections, or Radon transform, is illustrated in FIGS. 6A-6C, in which FIG. 6A illustrates a standard Radon transform or sinogram and FIG. 6B illustrates the sampling recommended for a central region of an image. While this center sampling technique greatly reduced the radiation levels by as much as 90%, this technique was designed for parallel beam geometries and is not completely feasible for fan-beam geometries. In particular, for standard fan-beam CT machines, the sampling is 0-1, meaning that the x-ray tube would either have to be shut off or modulated very quickly to accomplish this type of sampling.

The present disclosure will now outline the refinements and improvements for a fan-beam geometry, as well as a parallel beam geometry. Accordingly, FIG. 6C illustrates an exemplary sampling scheme for localized imaging, in accordance with various embodiments of the present disclosure. As opposed to the center sampling scheme (see FIG. 6B), an exemplary sampling technique in accordance with embodiments of the present disclosure (see FIG. 6C) is for an off-centered region. This off-centered type of sampling scheme will easily work with fan-beam geometries.

As described previously, earlier methods concentrated on 0-1 sampling. Namely, a linear x-ray beam would be either sampled or not sampled. The present disclosure will relax this condition and attempt to find an optimal solution to minimize radiation. Thus, in various embodiments, techniques of the present disclosure will either sample at the necessary high-dosage rate, which is required for appropriate SNR and resolution in the ROI, or a variable lower-dosage rate, which is all that is necessary outside the ROI.

This optimal solution to this problem is necessarily better than the optimal solution to the 0-1 sampling problem. Any time more variables are added to an optimization problem, the solution necessarily gets better. Moreover, this will allow us to design the system in a way that is easily implementable in hardware. In one embodiment, static or non-adaptive/dynamic attenuating filters are used in front of the x-ray transmitter, to alter the beam for the appropriate reduced dosage.

This approach is now illustrated, both mathematically and visually. Assume for now that the region of interest is circular (with radius $r_1$) and that the x-ray scanner is centered on the center of the circle when θ=0. Then, there is a distance d from the isocenter of the scanner to the center of the ROI, in which the ROI is assumed to be a circle with radius $r_1$. As the x-ray transmitter moves with θ, the center of the circle will then be a distance d(θ)=dsin(θ) off of the center of the gantry. Thus, we want to gather a full data set of the x-rays which pass through the ROI, which represent a first data set $P_f^h(\theta, r)=P_f(\theta, r)$ where $0\leq\theta\leq\pi$ and $r \in$ [dsin(θ)−$r_1$, dsin(θ)+$r_1$]. This first data set is gathered with full radiation dosage, just as if you were going to image the whole slice. Therefore, it will have a relatively high SNR. The notation $P_f^h(\theta,r)$ recognizes that this data will be used to reconstruct the high frequency details of the image.

A second data set is then gathered from all of the lines or projections which did not intersect the region of interest. The second data set is a low frequency data set $P_f^l(\theta, r)=P_f(\theta,r)$, where $r \notin$ [dsin(θ)−$r_1$, dsin(θ)+$r_1$]. This low frequency data set is gathered with minimal radiation, will have very low SNR, and will only be needed to reconstruct the low frequency portion of the image and will not affect the final image in the ROI.

The data sets are combined to get an approximate, noisy sinogram or Radon transform $P_f(\theta, r) \approx P_f^h(\theta, r) + P_f^l(\theta, r)$, noting that all of the Radon transform has been sampled, some of it at high SNR and some at low SNR. The final reconstruction will be $$f(\vec{x}) \approx \int_0^\pi (P_f(r, \theta) * k(r)))(\vec{x} \cdot \vec{\theta}) d\theta, \quad (12)$$

$$= \int_0^\pi (P_f(r, \theta) * k_h(r)))(\vec{x} \cdot \vec{\theta}) d\theta + \int_0^\pi (P_f(r, \theta) * k_l(r)))(\vec{x} \cdot \vec{\theta}) d\theta$$

$$= \int_0^\pi (P_f^h(r, \theta) * k_h(r) + P_f^l(r, \theta) * k_h(r)))(\vec{x} \cdot \vec{\theta}) d\theta +$$

$$\int_0^\pi (P_f^h(r, \theta) * k_l(r) + P_f^l(r, \theta) * k_l(r)))(\vec{x} \cdot \vec{\theta}) d\theta$$

The first term $P_f^h(r, \theta) * k_h(r)$ is the term which will yield most of the high resolution image, and is highly sampled through the ROI. This is the foundation of the reconstruction. The second term $P_f^l(r, \theta) * k_h(r)$ will be essentially zero, since it is the convolution of high frequency data versus a low frequency kernel. The third term $P_f^h(r, \theta) * k_l(r)$ is essentially zero for the same reason—it is the convolution of low frequency data and a high frequency kernel. The last term, $P_f^l(r, \theta) * k_l(r)$ is the low frequency term which is essential. At first one might think that this would end our ability to accomplish the task of lowering the radiation levels, since these low frequency terms are global and cannot be measured locally. We must remember the structure of the Radon transform to minimize this non-local information.

Thus, there is a very high SNR estimate for the high frequency components inside the ROI. We must recall the structure of the Radon transform to realize why the low frequency component is not affected by the low SNR estimates. Recall from Equation (11) that the low frequency components are only affected by low frequency sines and cosines with respect to θ or the Fourier transform $$f_l(s\vec{\theta}) = \sum_{l=0}^{N-1} l^{-1} J_l(s) h_l(\theta),$$

with N being very small. Restating this, if you look at the Fourier transform from a polar viewpoint, the small circular components are controlled by very low-order sines and cosines. Therefore, since we are estimating very few parameters in the low frequency component and have a great number of data samples, the law of large numbers will yield a very solid estimate for the low frequency component. This can be accomplished even if this data is gathered at very low SNR levels, i.e. with very little radiation.

Figure 7A:
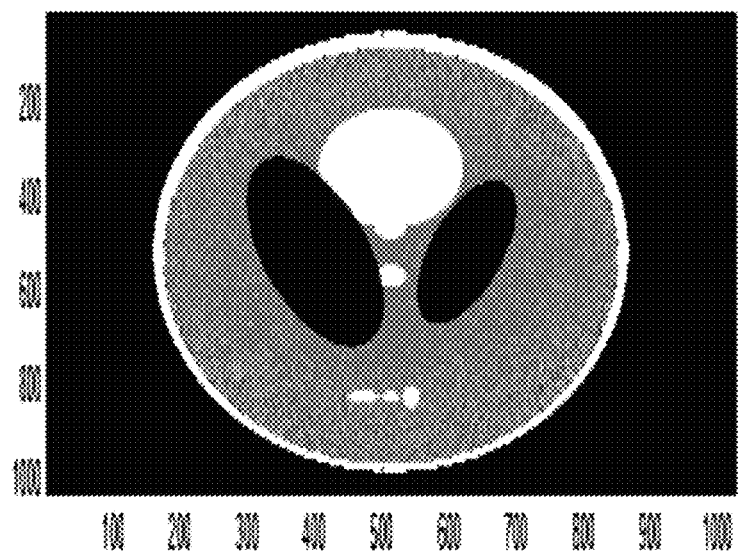
FIGS. 7A-7F are diagrams illustrating image reconstructions for a central region and a non-central region from full and reduced data sets in accordance with embodiments of the present disclosure.
Figure 7B:
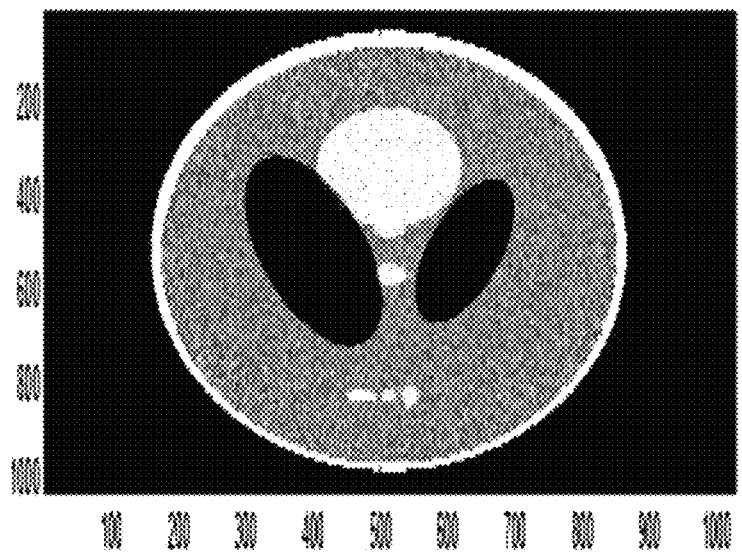
Figure 7C:
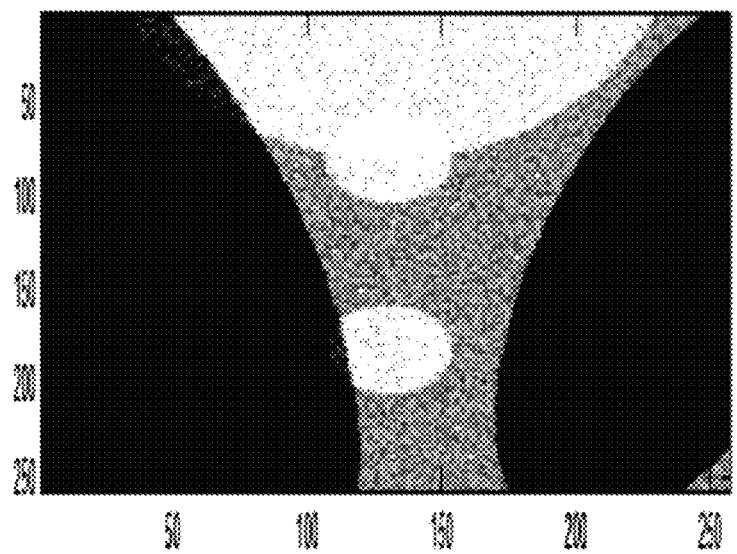
Figure 7D:
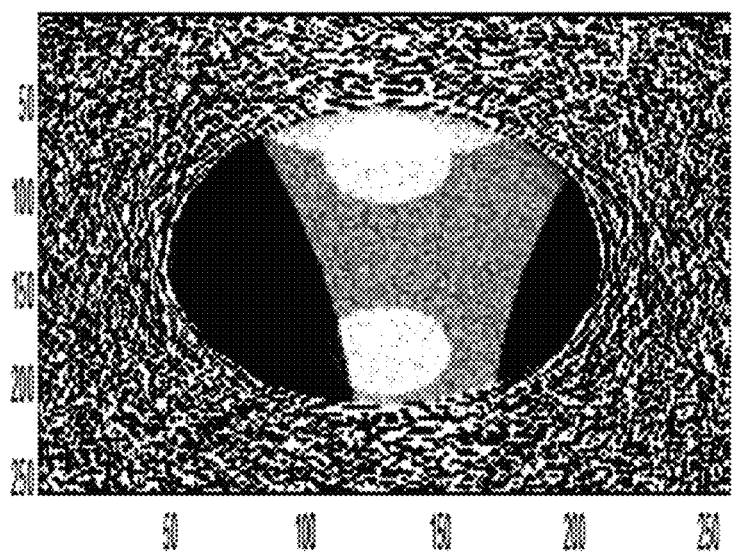
Figure 7E:
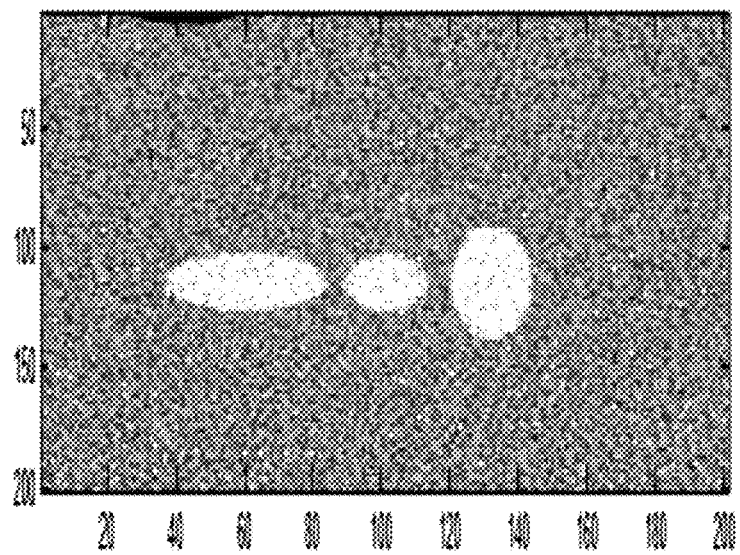
Figure 7F:
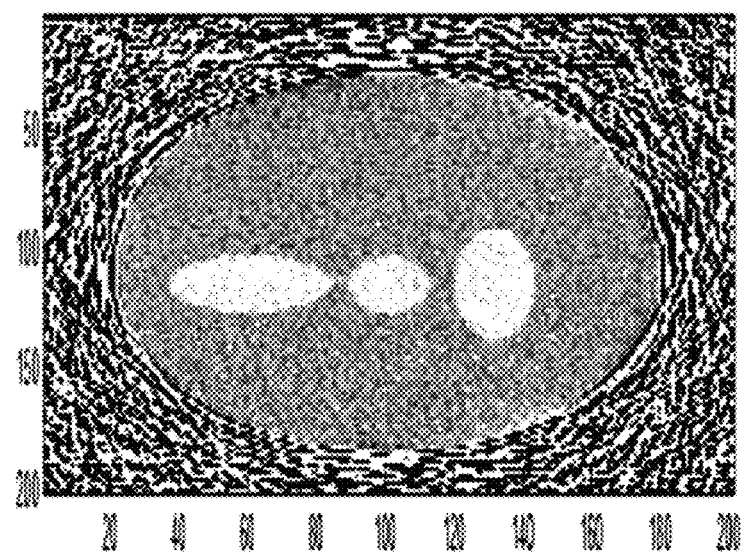

This process is illustrated in FIGS. 7A-7F, in which FIGS. 7A-7B illustrate the radiation exposure recommended for a central region and a non-central region of an image. The original non-noise related reconstruction is shown at FIG. 7A and the noisy reconstruction is shown at FIG. 7B. As opposed to the 0-1 sampling scheme, the adaptive sampling method in accordance with embodiments of the present disclosure is designed for arbitrary geometries and can be implemented in a fan-beam geometry. Accordingly, FIGS. 7C-7D show the ROI reconstructed with a full data set (in FIG. 7C), and with the reduced data set (in FIG. 7D) in accordance with embodiments of the present disclosure. Additionally, FIGS. 7E-7F show an off-center ROI reconstructed from a large data set (in FIG. 7E) and small data sets (in FIG. 7F) in accordance with embodiments of the present disclosure. The radiation reduction was 92% for FIGS. 7D and 7F. A natural question might be "Do we really need to process any data which doesn't pass through the ROI?"

Figure 8A:
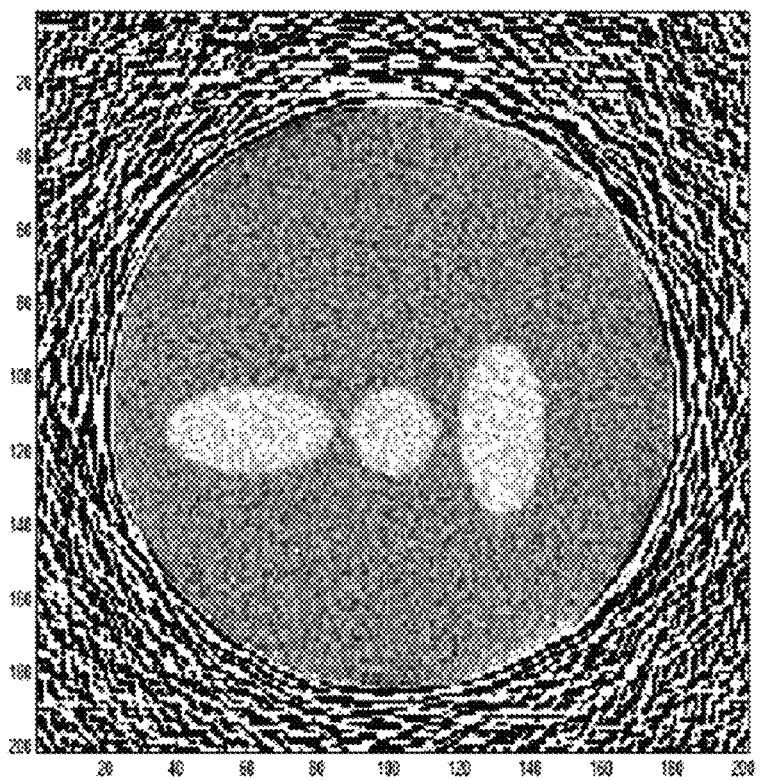
Figure 8B:
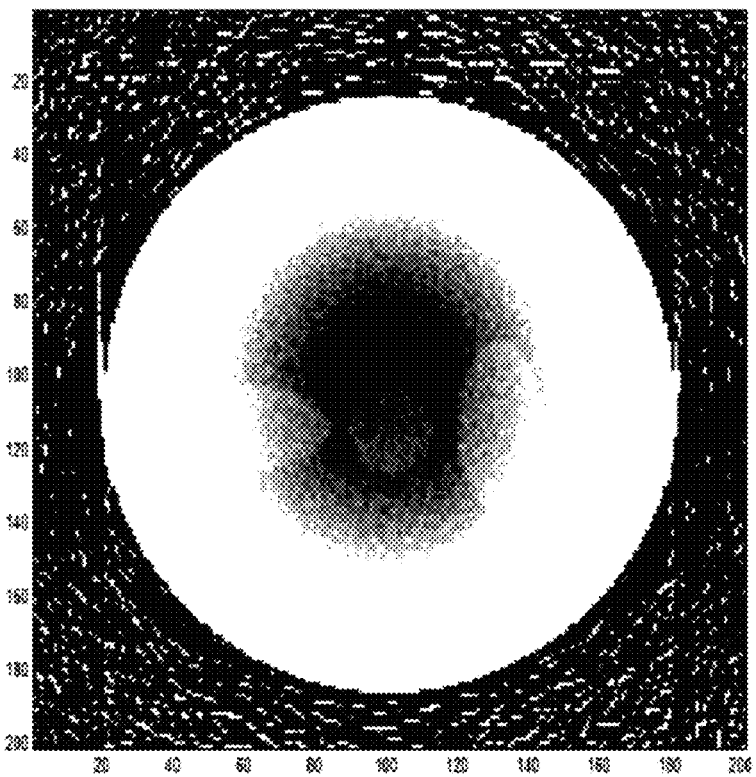

To address this inquiry, FIGS. 8A-8B are diagrams illustrating a reconstruction using nearly-local data and completely local data. FIG. 8A is the localized reconstruction, as was shown in FIGS. 7A-7F, using nearly-local data. FIG. 8B is the reconstruction with totally local data, ignoring the steps for the localized data (nearly-local), as outlined above. From a review of FIG. 8B, it is apparent that the quality of image reconstruction for FIG. 8B is not on par with the quality of the image reconstruction for FIG. 8A.

Noise analysis and modification can be done on the unprocessed raw data which comes from the photon detectors. Let's recall Equation (1):

$$P_f(r, \vec{\theta}) = \int f(r\vec{\theta} + t\vec{\theta}^\perp) dt,$$

which is central to CT.

The data $P_f(r, \vec{\theta})$ is actually pre-processed in the following way. The actual raw data from the CT detectors, $P_f(r, \vec{\theta})$ is given by $$R_f(r, \vec{\theta}) = \exp(-P_f(r, \vec{\theta})).$$

Thus, the utilized data is gained by the expression $$P_f(r, \vec{\theta}) = -\ln(R_f(r, \vec{\theta})).$$

The reason that we want to step back to $R_f(r, \vec{\theta})$ is that the statistics of measuring $R_f$ are very well known. A CT machine sends photons through the medium (i.e. the patient) along a straight line, and the resulting arrivals are classic Poisson arrivals with their mean being (the natural log of) the actual desired result $P_f(r, \vec{\theta})$ and a variance which decreases according to how many photons are sent. Thus, lower radiation measurements of $R_f$ are just noisier in a classical Poisson measurement process.

For the following trials, data is acquired by imaging a human cadaver at 4 different radiation dose levels: 2 milligray (mGy), 8 mGy, 18 mGy, and 60 mGy. To put perspective on this, most clinical abdominal CT scans reconstructed with filtered backprojection will use around 18-20 mGy for adults, with 60 mGy far exceeding the norm. Scanners using iterative reconstruction algorithms may use closer to 8 mGy for the same scan. For children or infants, lower doses such as 8 mGy or 2 mGy are routinely used. This is partially due to two reasons: 1) The much smaller body size, meaning its far easier to penetrate through the body and 2) Increased attention to dose reduction, due to the higher radiosensitivity of children and the longer lifespan they have in which to develop a cancer with a long latent period.

For these trials, the CT scanner that was used did not permit further dose reduction below 2 mGy. Future clinical implementation of this technique will require the development of an adjustable collimator mechanism, which will allow us to reduce the ionizing radiation exposure to areas outside the ROI to about 10% or less of the normal clinical dose. For the present disclosure, using 18 mGy for the region of interest (ROI) and 2 mGy for the exterior, non-ROI projections adequately simulates the ROI/non-ROI dose ratio that is anticipated to perform well with the focused tomography method.

For the clinical trials, measurements are made at 18 mGy for the region of interest (ROI) and at 2 mGy for the exterior, non-ROI projections. For simplicity two different modes are specified for the acquired images. The first is denoted by Focused Tomography 1 (FCT1) by which the present disclosure uses the lower dosage measurement outside the ROI and the higher dosage measurements inside the ROI with no transition region between them. The second is denoted by Focused Tomography 2 (FCT2) by which we have a smooth windowed transition or ramp between the lower dosage and the higher dosage measurements.

Figure 9:
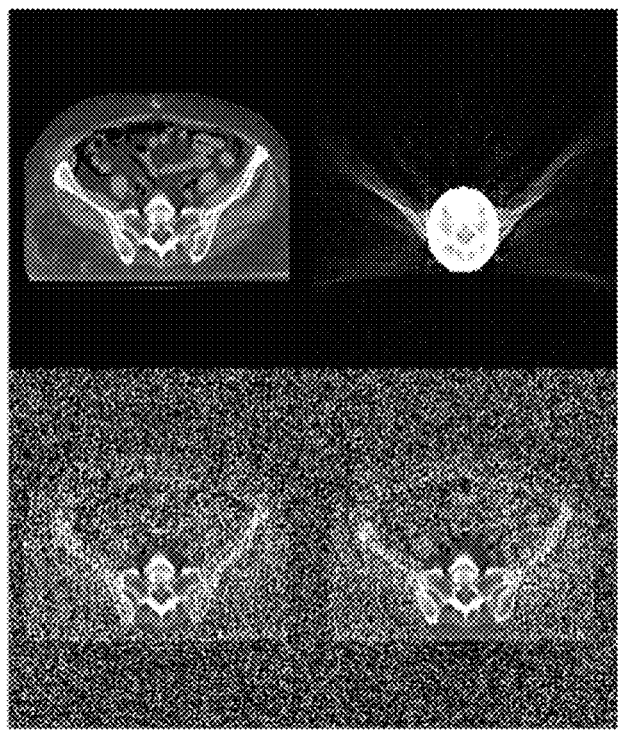
FIG. 9 shows images provided from an exemplary focused CT methodology with a region of interest (ROI) around the sacrum in accordance with the present disclosure. The original non-noise related reconstruction is at the top left and the reconstruction with totally local data is seen on the top right. The bottom row shows the reduced radiation methods with a first mode of focused computed tomography (FCT1) on the left and a second mode of focused computed tomography (FCT2) on the right.

The first clinical study is of the sacrum which is illustrated in FIG. 9. Injuries to the sacrum and lumbar spine car accidents or falls have devastating consequences affecting mobility and the control of bladder and bowel function in both the young and old. Injuries to the sacrum may result in the need for surgery and repeated CT imaging. CT imaging of the sacrum involves irradiating the entire pelvis, which includes radiosensitive tissues such as the colon, bladder, reproductive organs, and red bone marrow in the pelvis and hips.

As used in acquisition of the images of FIG. 9, an exemplary focused CT methodology with an ROI around the sacrum results in a reduction of radiation levels by approximately 80%. As opposed to the 0-1 sampling scheme, this adaptive sampling method was designed for arbitrary geometries, and can be implemented in a fan-beam geometry. The original non-noise related reconstruction is the top left of FIG. 9 and the reconstruction with totally local data is seen on the right. The bottom row of FIG. 9 shows the reduced radiation methods with FCT1 on the left and FCT2 on the right.

Figure 10:
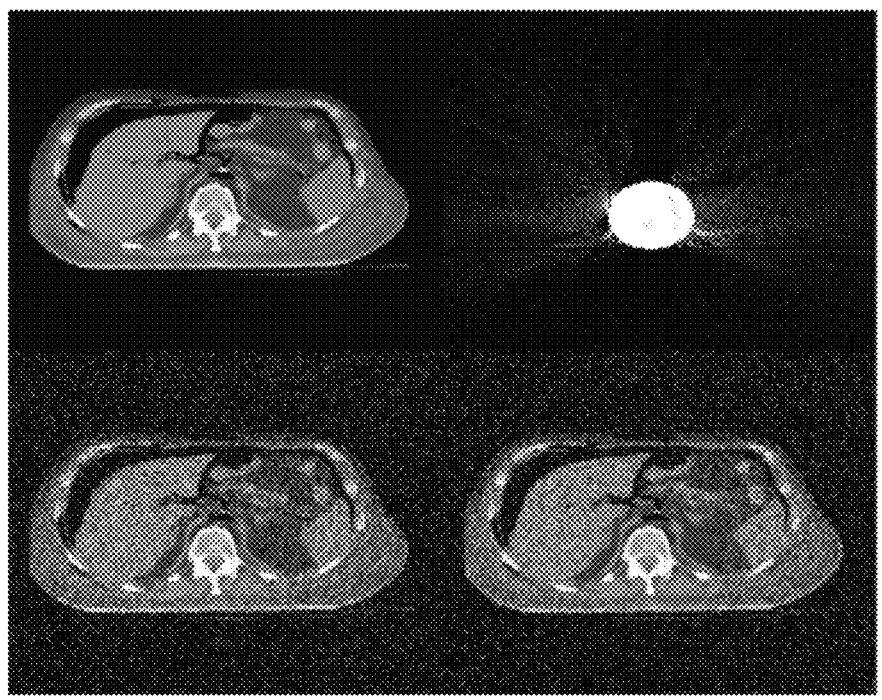
FIG. 10 shows images provided from an exemplary focused CT methodology with an ROI around another thoracic spine. The original non-noise related reconstruction is at the top left and the reconstruction with totally local data is seen on the top right. The bottom row shows the reduced radiation methods with FCT1 on the left and FCT2 on the right.

A second clinical study is of the lower thoracic spine which is illustrated in FIG. 10. The spine is crucial for long-term health and mobility and is surrounded by radiosensitive organs that are exposed to radiation during CT imaging: the lungs, stomach, liver, and breast in the thoracic region; and the colon, bladder and reproductive organs in the lumbar regions. Sensitive red bone marrow is also exposed in all areas of spine imaging, e.g. in the shoulders, ribs, sternum, and pelvis.

As used in acquisition of the images of FIG. 10, an exemplary focused CT methodology with an ROI around another thoracic spine results in radiation levels by approximately 80%. As opposed to the 0-1 sampling scheme, this adaptive sampling method was designed for arbitrary geometries and can be implemented simply in a fan-beam geometry. The original non-noise related reconstruction is at the top left of FIG. 10 and the reconstruction with totally local data is seen on the right. The bottom row of FIG. 10 shows the reduced radiation methods with FCT1 on the left and FCT2 on the right.

Accordingly, FIG. 10 demonstrates that adequate image quality of the spine can be obtained with a dose reduction of about 80%. As for the sacrum, multiple CT scans will often be used for investigation and then evaluation treatment options and outcomes in the spine, thus multiplying the benefit.

Figure 11:
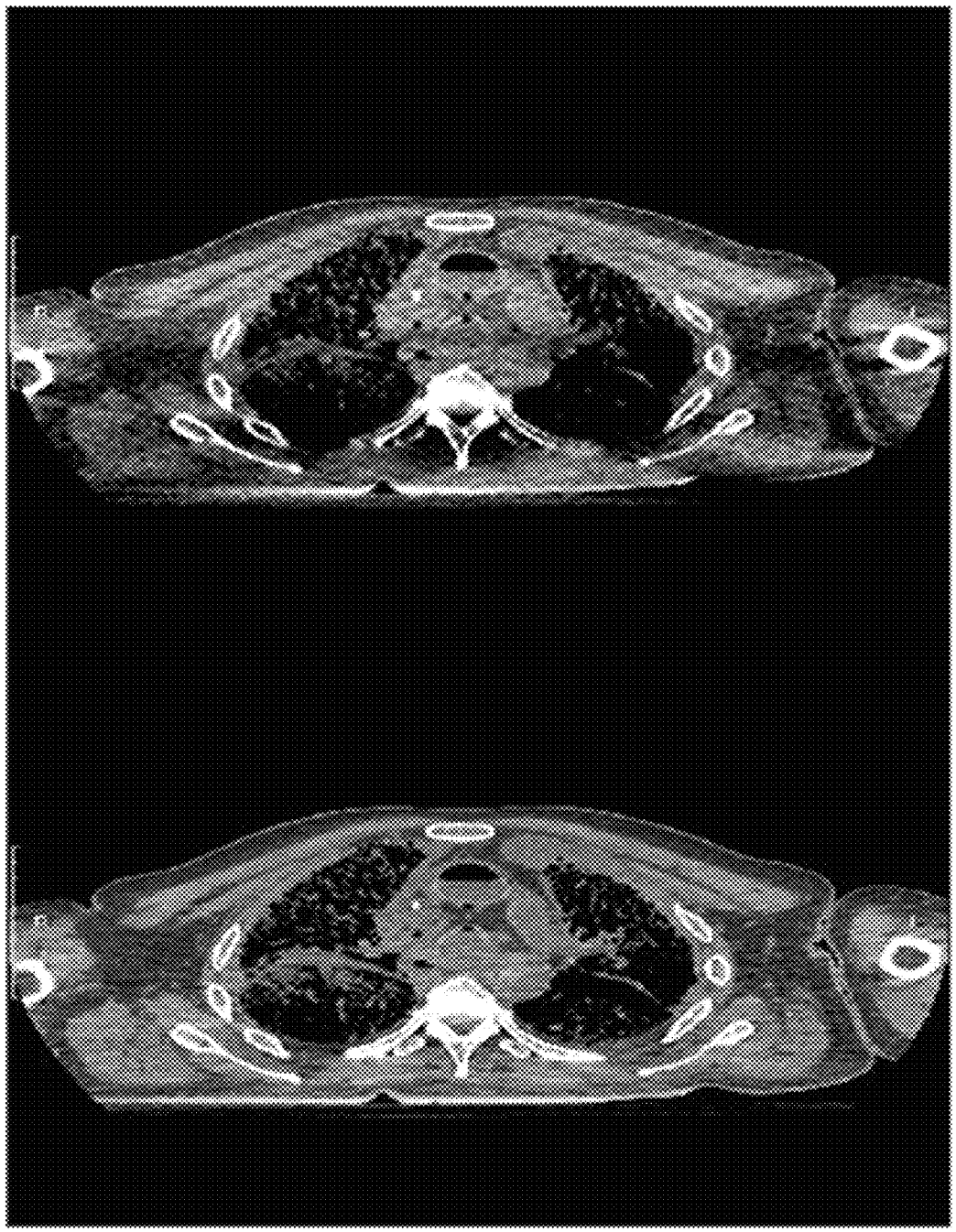
FIG. 11 shows two images of a cadaver taken at 1.7 mGy (top) and at 17 mGy (bottom) in accordance with the present disclosure.
Figure 12:
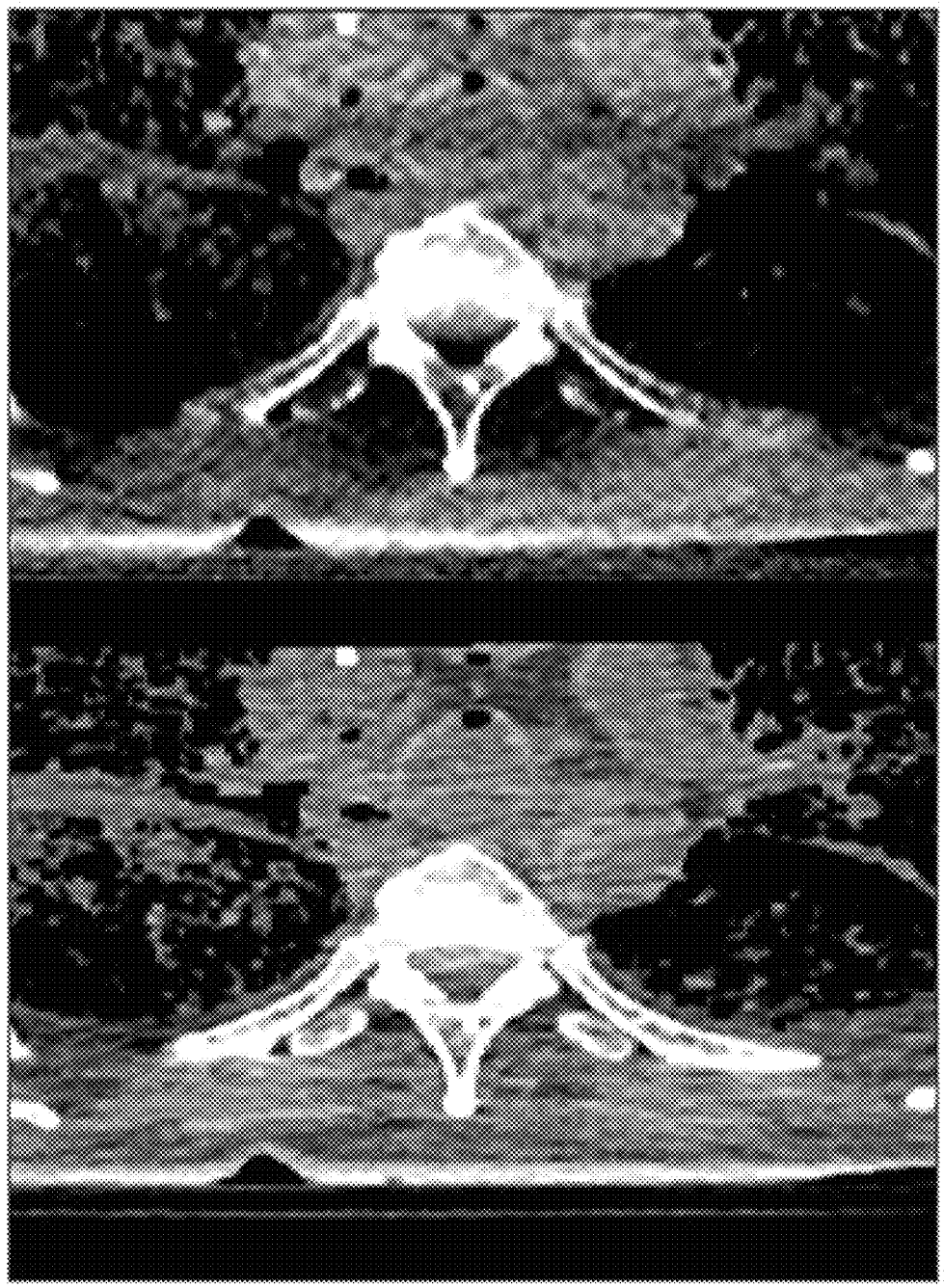
FIG. 12 shows two close-up images from the images in FIG. 11 in accordance with the present disclosure.

FIG. 11 illustrates two images of the same cadaver above. The top one was taken at 1.7 mGy and the bottom at 17 mGy. While they are clearly the same, it is noted that the detail from the 1.7 mGy image is not nearly that of the 17 mGy image. FIG. 12 illustrates the close-up images from the images in FIG. 11. Again, it is noted that that there is not nearly the detail in the 1.7 mGy image as in the 17 mGy image. The present disclosure desires to preserve this level of detail while reducing the radiation levels significantly.

Figure 13:
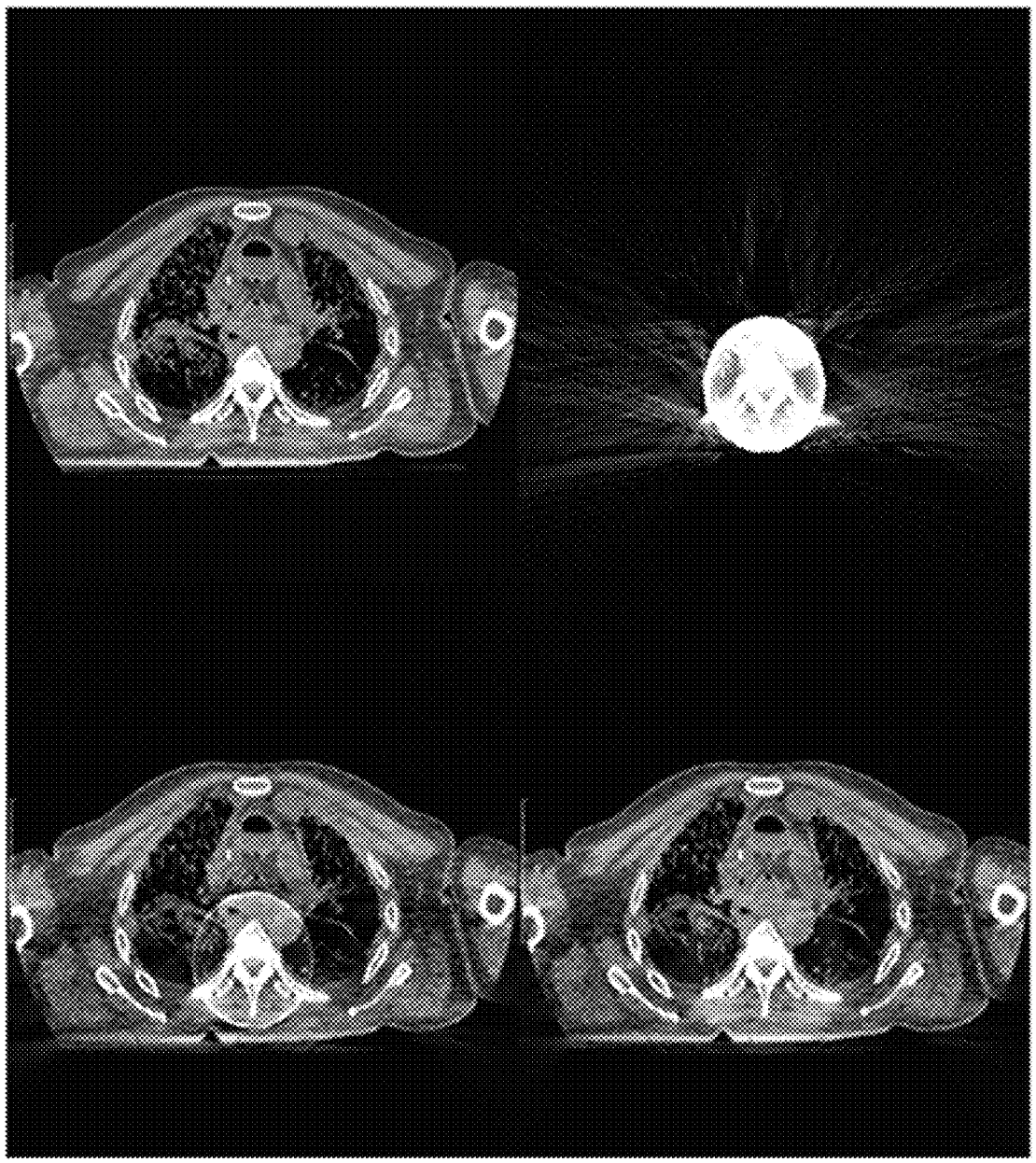
FIG. 13 shows images provided from exemplary focused tomography techniques in accordance with various embodiments of the present disclosure. An original 17 mGy image is at the top left; an image from totally local data is at the top right; the image at the bottom left is a result of combining the 17 mGy data through the region of interest and the 1.7 mGy data outside the ROI; and the image at the bottom right is a result of performing compensation to avoid Gibbs ringing.

Next, FIG. 13 shows images provided from exemplary focused tomography techniques. All images are shown with the same thresholds for display. The original 17 mGy image is at the top left of the figure. The image from totally local data, i.e. only integrals through the region of interest, is at the top right. The images on the bottom row are two varieties of an exemplary focused tomography technique in accordance with various embodiments. In particular, the bottom left image is a result of combining the 17 mGy data through the region of interest and the 1.7 mGy data outside the ROI, in which it is noticed that there is still some Gibbs ringing around the ROI. For the image on the bottom right of the figure, compensation is performed to avoid the Gibbs ringing, and as a result, the image is nearly exact in the ROI with the original 17 mGy image.

Figure 14:
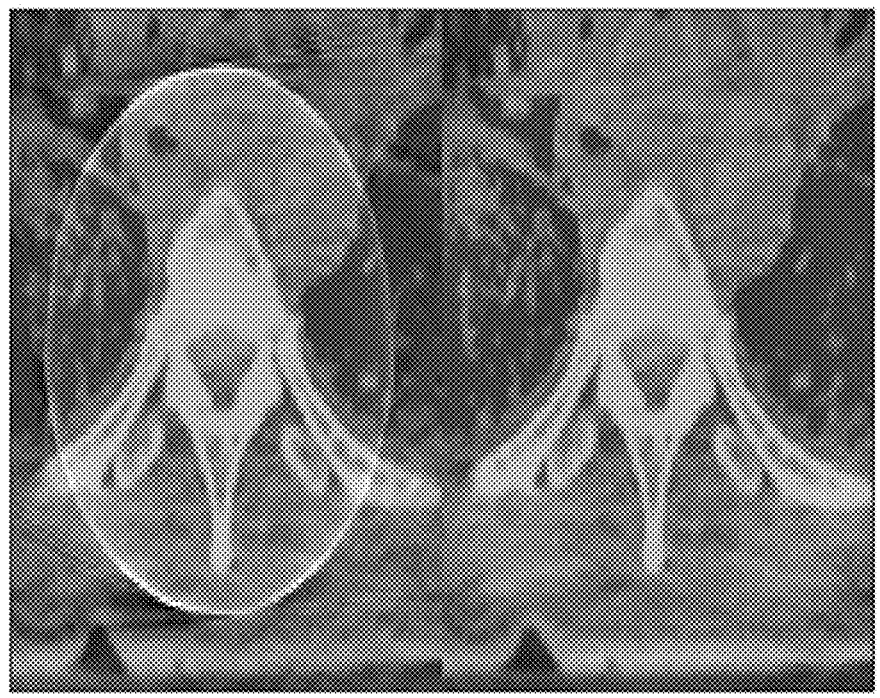
FIG. 14 shows closeup images of the two bottom examples in FIG. 13.
Figure 15:
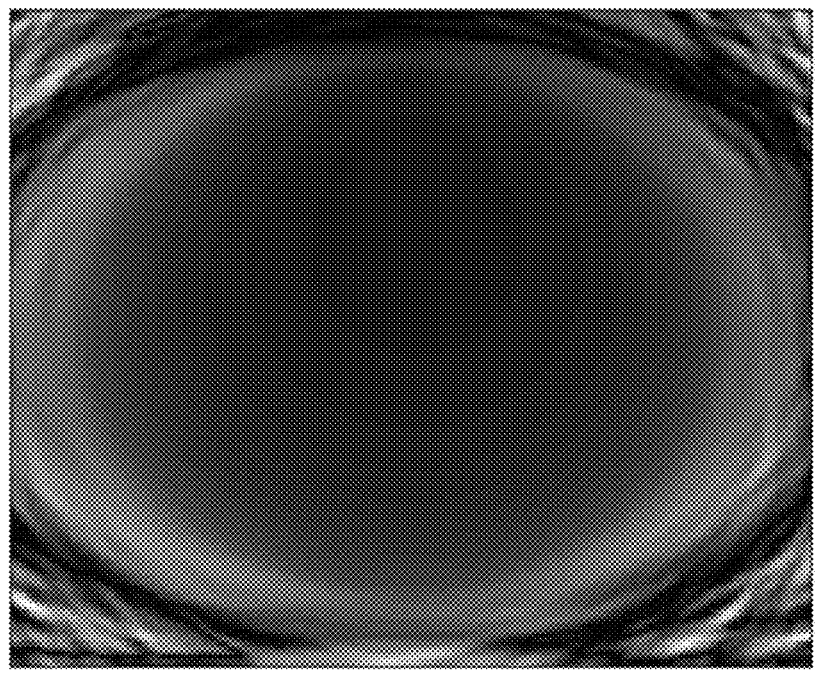
FIG. 15 is an image showing a difference between the result of FIG. 13 at the bottom left example and the original interest.

FIG. 14 shows closeups of the ROI's from the two bottom examples in FIG. 13. It is noted that Gibbs ringing is present on the image on the left. On the image on the right, compensation techniques have been used to alleviate the Gibbs ringing. FIG. 15 shows the difference between the results from the bottom left of FIG. 13 and the original interest. It is noted that there begins to be a significant difference outside the ROI, but, within the ROI, the mean square error (MSE)=0.0041, which would generally be below or at the threshold of most display mechanisms.

Figure 16:
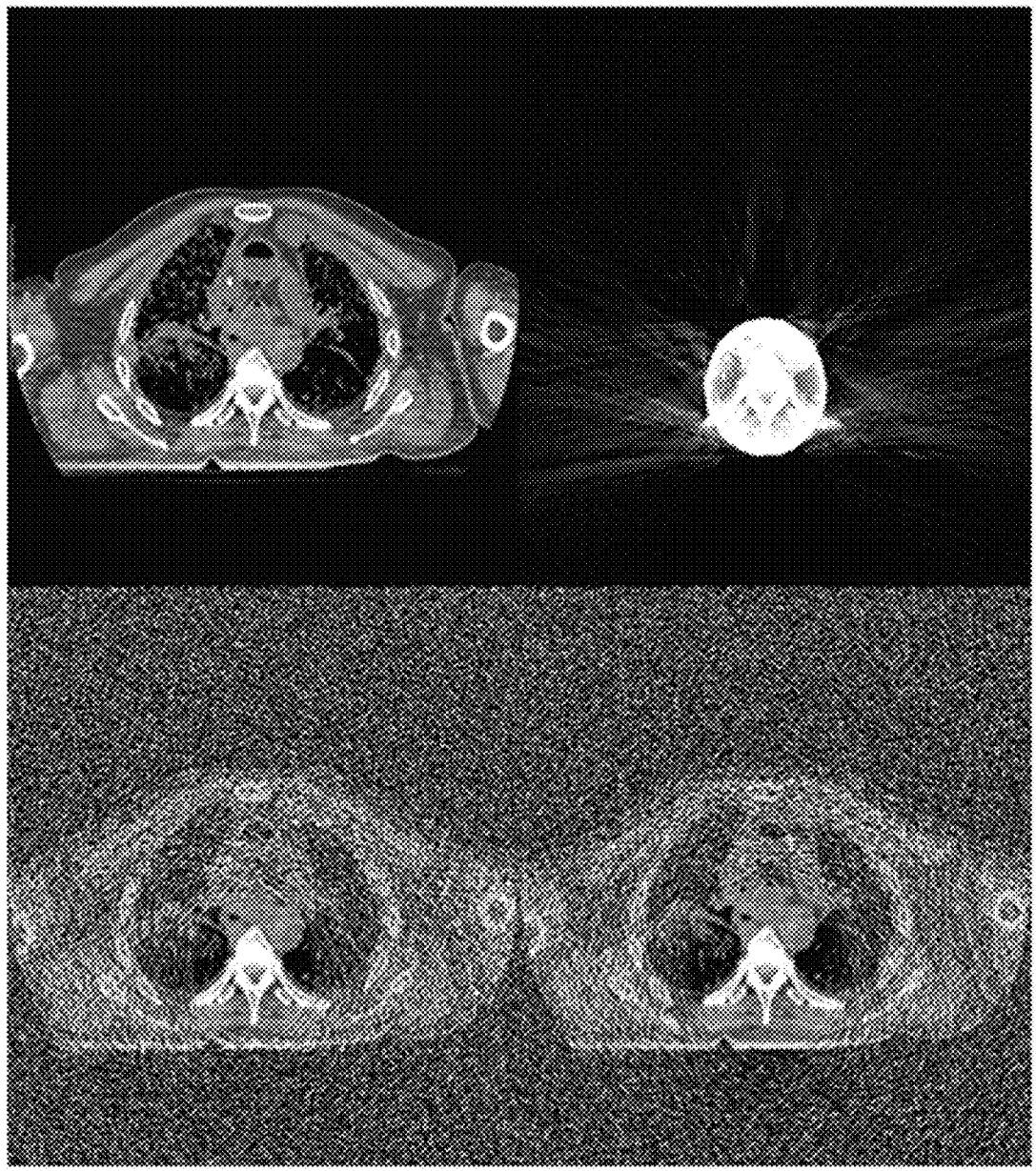
FIG. 16 shows images provided from exemplary focused tomography techniques at a lower off-ROI exposure rate in accordance with various embodiments of the present disclosure. An original image is at the top left; an image from totally local tomography data is at the top right; the image at the bottom left is a result of reducing the off-ROI radiation levels; and the image at the bottom right is a result of performing compensation to avoid Gibbs ringing.

FIG. 16 shows images provided from exemplary focused tomography techniques at a lower off-ROI exposure rate in accordance with various embodiments of the present disclosure. An original image is at the top left; an image from totally local tomography data is at the top right; the image at the bottom left is a result of reducing the off-ROI radiation levels; and the image at the bottom right is a result of performing compensation to avoid Gibbs ringing. Since current scanners will not allow us to lower our off-ROI radiation levels to breaking point of an exemplary algorithm in accordance with the present disclosure, the reduction in radiation levels is illustrated by adding noise to the off-ROI scans. These scans suggest that the algorithm would work with an off-ROI radiation dose even lower than 10% of the full ROI dose.

Figure 17:
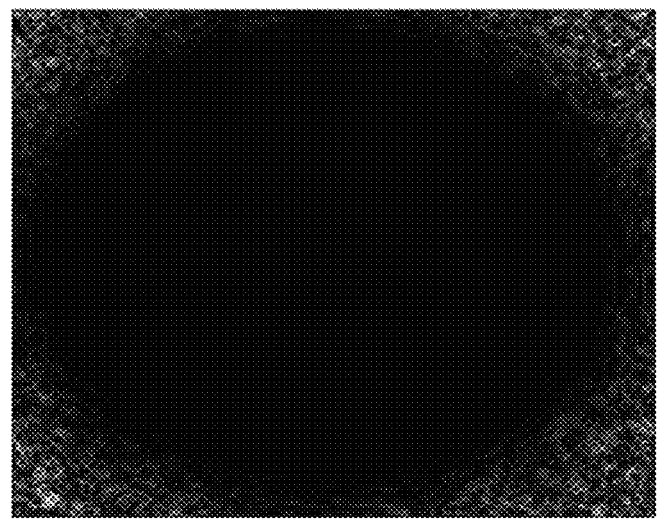
FIG. 17 is a difference image from the scans in FIG. 16 that shows nearly no variance within the ROI.
Figure 18:
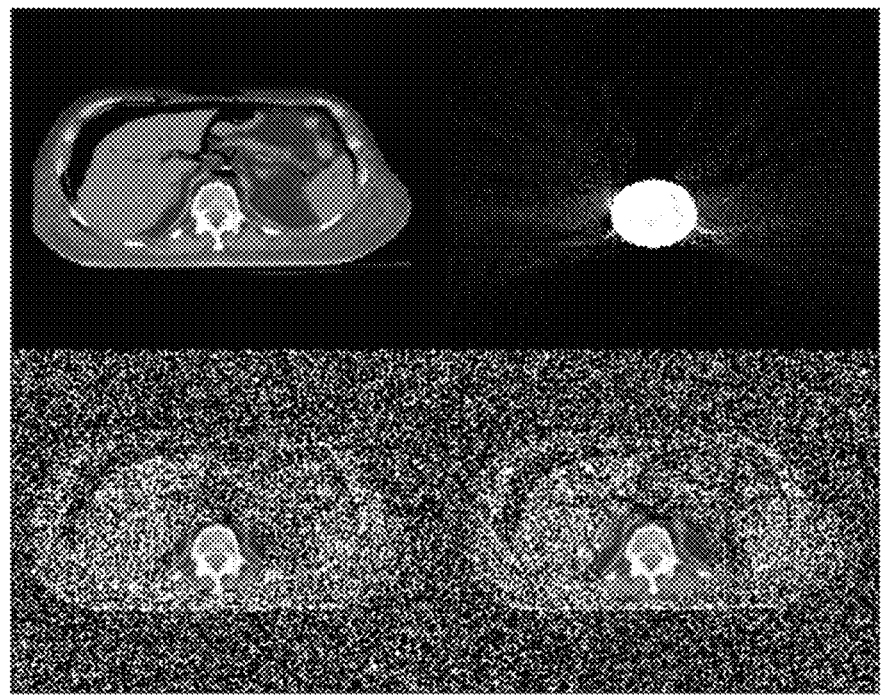
FIG. 18 shows images provided from an exemplary focused CT methodology with an ROI around a thoracic spine. The original non-noise related reconstruction is at the top left and the reconstruction with totally local data is seen on the top right. The bottom row shows the reduced radiation methods with FCT1 on the left and FCT2 on the right.
Figure 19:
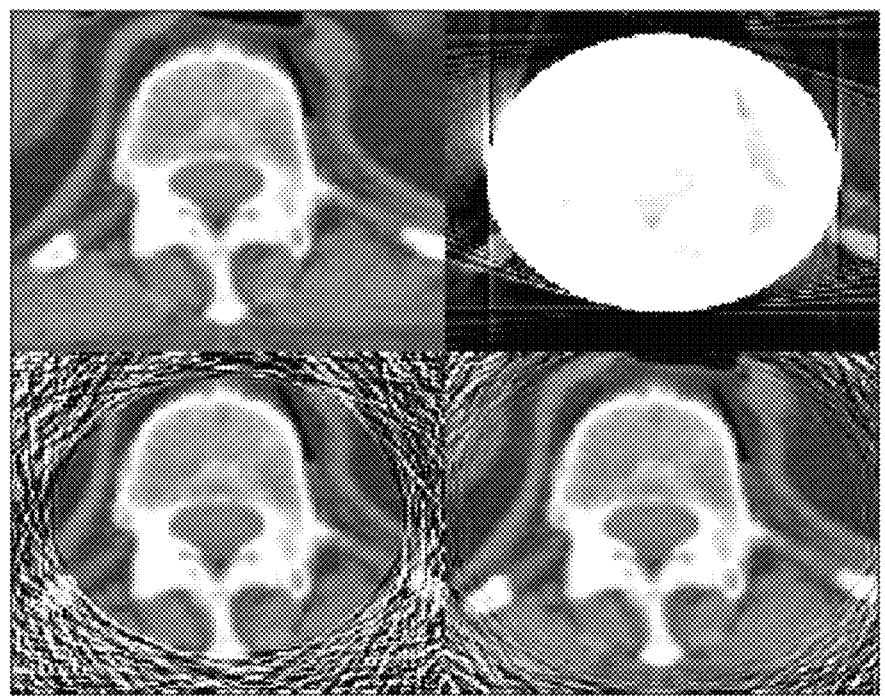
FIG. 19 shows images provided from an exemplary focused CT methodology with an ROI around a thoracic spine. The original non-noise related reconstruction is at the top left and the reconstruction with totally local data is seen on the top right. The bottom row shows the reduced radiation methods with FCT1 on the left and FCT2 on the right.

FIG. 17 shows a difference image from the scans in FIG. 16 that shows nearly no variance within the ROI. The MSE in this area was once again very low, at 0.00024. This illustrates that radiation can be nearly eliminated from off-ROI region scans through this technique. In FIGS. 18 and 19, it is illustrated that even lower doses radiation outside the region of interest can be used with nearly perfect results, although there is a law of diminishing return. It is believed that the radiation level is reduced by approximately 85% in these images. The images are of a spine with much lower dosage outside the ROI. This success is believed to be due to the low frequency coefficients being nearly invariant on standard human scans.

Referring to FIG. 18, images are presented that illustrate an exemplary focused CT methodology with an ROI around a thoracic spine. In these images, off-ROI radiation levels are utilized which were much lower than those of FIG. 10. This results in a reduction of radiation levels by approximately 85%. As opposed to the 0-1 sampling scheme, this adaptive sampling method was designed for arbitrary geometries and can be implemented simply in a fan-beam geometry. The original non-noise related reconstruction is at the top left of the figure and the reconstruction with totally local data is seen on the right. The bottom row of the figure shows the reduced radiation methods with FCT1 on the left and FCT2 on the right.

Referring next to FIG. 19, images are presented that illustrate an exemplary focused CT methodology with an ROI around a thoracic spine. Closeups of the ROI are illustrated in the figure. In these images, off-ROI radiation levels are utilized which were much lower than those of FIG. 10. Radiation levels are reduced by approximately 85%. As opposed to the 0-1 sampling scheme, this adaptive sampling method was designed for arbitrary geometries and can be implemented simply in a fan-beam geometry. The original non-noise related reconstruction is at the top left of the figure, and the reconstruction with totally local data is seen on the top right. The bottom row shows the reduced radiation methods with FCT1 on the left and FCT2 on the right.

Figure 20:
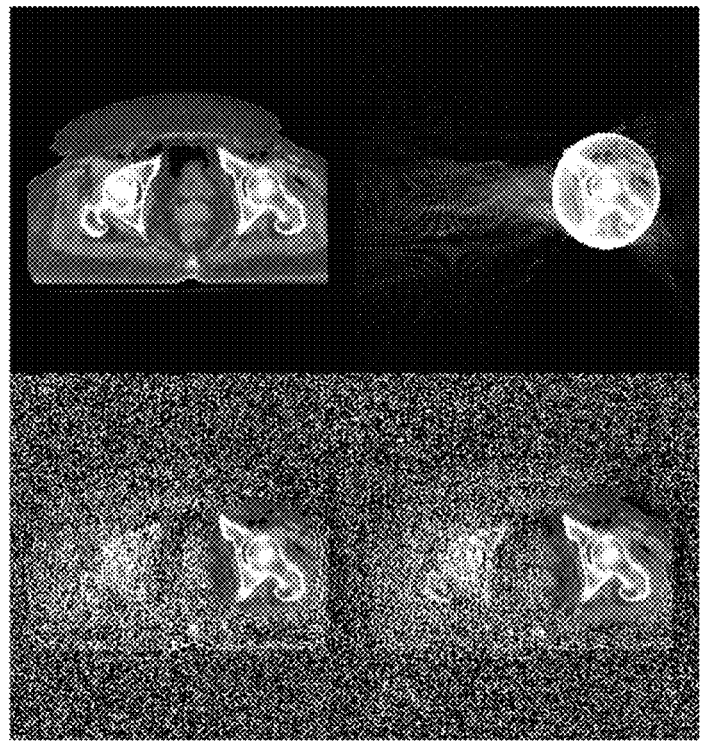
FIG. 20 shows images provided from an exemplary focused CT methodology with and ROI around a hip. The original non-noise related reconstruction is at the top left and the reconstruction with totally local data is seen on the right. The bottom row shows the reduced radiation methods with FCT1 on the left and FCT2 on the right.
Figure 21:
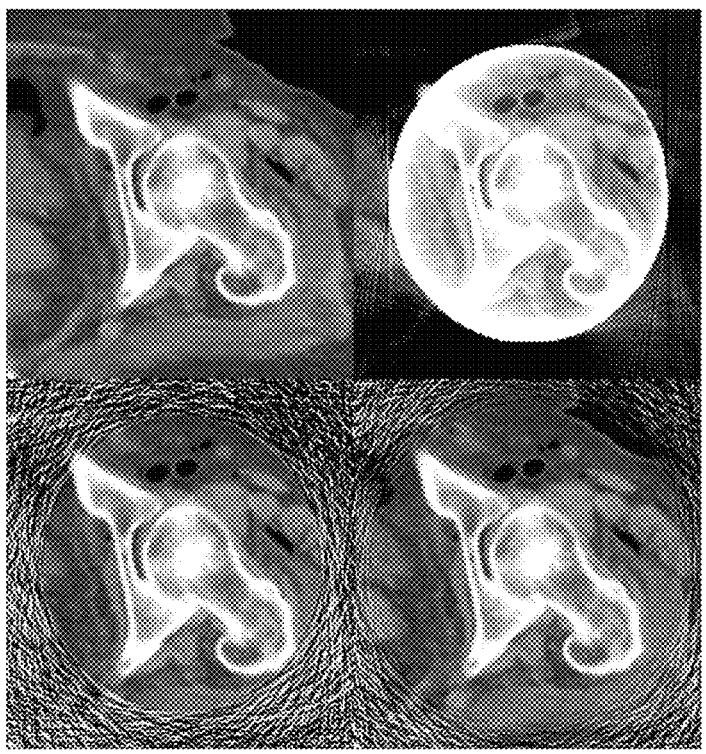
FIG. 21 shows images provided from an exemplary focused CT methodology with an ROI around a hip. The original non-noise related reconstruction is at the top left of the figure and the reconstruction with totally local data is seen on the top right. The bottom row shows the reduced radiation methods with FCT1 on the left and FCT2 on the right.

The same techniques are illustrated in FIGS. 20 and 21 on a hip socket. Once again, remarkably perfect images of the ROI are retrieved a with very low dosage. For FIG. 20, images are provided from an exemplary focused CT methodology with and ROI around a hip. This results in a reduction of radiation levels by approximately 85%. As opposed to the 0-1 sampling scheme, this adaptive sampling method was designed for arbitrary geometries and can be implemented simply in a fan-beam geometry. The original non-noise related reconstruction is at the top left of the figure, and the reconstruction with totally local data is seen on the right. The bottom row shows the reduced radiation methods with FCT1 on the left and FCT2 on the right.

For FIG. 21, images are provided from an exemplary focused CT methodology with an ROI around a hip. Closeups of the ROI are illustrated in the figure. Radiation levels are reduced by approximately 85%. As opposed to the 0-1 sampling scheme, this adaptive sampling method was designed for arbitrary geometries and can be implemented simply in a fan-beam geometry. The original non-noise related reconstruction is at the top left of the figure, and the reconstruction with totally local data is seen on the right. The bottom row shows the reduced radiation methods with FCT1 on the left and FCT2 on the right. The results of FIGS. 18-20 suggest that far less off-ROI radiation can be used than standard results would suggest. It is believed that this is due to the low frequency component of human CT images being fairly invariant.

To assess the comparative image quality of the two methods (i.e. full dosage ROI scanning and reduced dosage ROI scanning), various metrics can be utilized. The obvious first metric can be simple mathematical mean square error measurement. These measurements do not, however, generally yield a true measure of the image quality. Therefore, visual quality metrics can be utilized, which have been developed in computer vision over the past 15 years to assess the relative value of both methods. Finally, a significant number of qualified physicians, surgeons, and radiologists can be enlisted to view this work. The study can be made to be double blind by showing images within the ROI from both the full exposure and reduced exposure methods.

In various embodiments, static attenuation filters can be developed and used in conjunction with scanners, in accordance with various embodiments of the present disclosure. The static filters will focus the radiation on the ROI and eliminate unnecessary non-local radiation. These static filters will only be able to gather data on a centralized ROI. In various embodiments, adaptive filters may be used as alternatives to static filters.

Additionally, in various embodiments, designed filters will be active, gathering data through a non-centered ROI at near real-time gantry speeds. Cramer-Rao statistical bounds will be attempted to prove that minimal data sets are being used. Also, in various embodiments, designed filters will be fully automated, so that a physician can choose his/her ROI, and have the machine optimally reduce (e.g., via a controller device) the radiation dose in accordance with the present disclosure.

Accordingly, in one embodiment, a designed filter will be a static filter, in which we will look to build a filter, or filters, which will alter the output of the CT machine producing a desirable localized radiation profile. This is possible with a number of materials, such as aluminum, by merely adjusting the depth of the filter. A stable material which will not degrade under the radiation exposure and which can be made thin enough to not interfere with the gantry is used in certain embodiments. In one embodiment, a designed filter will be a mechanically active, materially static filter. Accordingly, after having a static filter design, the filter can be mechanically moved, keeping the focus of the radiation on the region of interest.

In the present disclosure, cylindrical ROIs are considered. This is consistent with the spine and shoulders, but perhaps not optimal for hip imaging. However, it is contemplated that the mechanically-active filter would be capable of essentially imaging any ROI, including non-cylindrical ROIs. The radiation reduction of an exemplary cylindrical system is very substantial. We do not imagine decreasing this by more than 2 or 3 times with more advanced methods.

The following describes the sequence of steps required to perform the novel method of focused computed tomography (CT) in one embodiment. In general, a computed tomography scanner features a ring or cylinder for a gantry, in which a subject is positioned. An x-ray tube and an x-ray detector are positioned opposite of each other and rotate around the gantry as x-ray images are acquired. A body scanning filter, such as bowtie filter, is generally positioned in front of the x-ray tube to shape the x-ray beam and reduce the range of x-ray energies that reach the subject, such as reducing the beam intensity at the periphery of the x-ray beam that is transmitted. Additionally, a static pre-patient collimator may be positioned between the filter and the patient. In accordance with the present disclosure, an additional adaptive collimator device can also be positioned between the pre-patient collimator and the patient.

Figure 22:
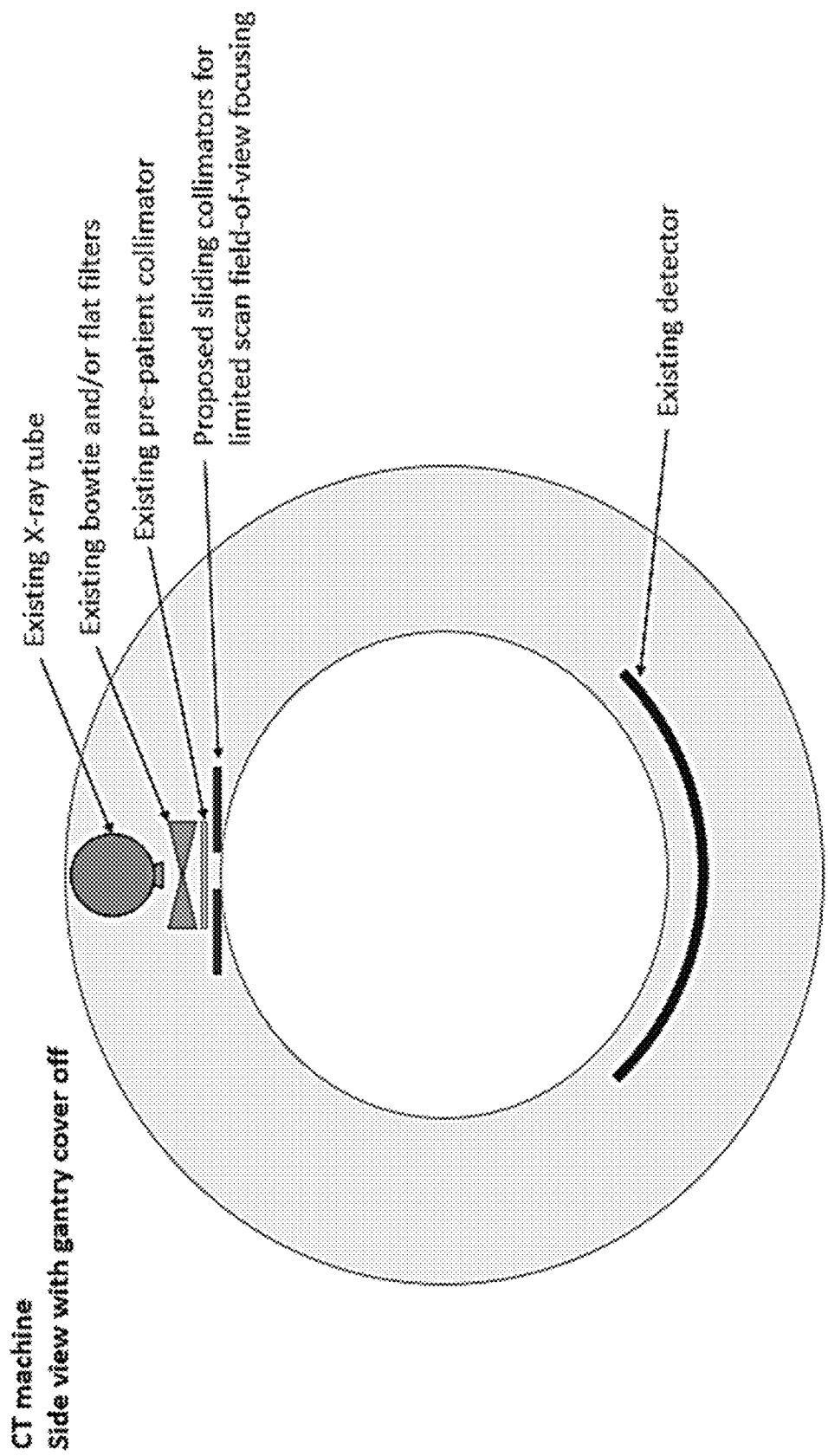
FIG. 22 is a diagram of a side view of an exemplary CT scanner showing the location of exemplary sliding collimators in relation to other key components of an exemplary CT system in accordance with embodiments of the present disclosure.

FIG. 22 illustrates an exemplary CT machine with the gantry cover off showing the addition of sliding collimators, in accordance with various embodiments of the present disclosure. The sliding collimators facilitate the creation of a limited scan field-of-view for the focused tomography reconstruction. In various embodiments, a movable collimator made from copper, tungsten, or a similar material, can be deployed to reduce the radiation. In various embodiments, the collimator is selected of an appropriate material with an atomic number to block approximately 90% of the radiation through the non-ROI region. The detailed specifications would depend on the beam quality of the most-commonly used x-ray tube potential. This collimator will adjust in size and position to center on the main ROI via continuous motion throughout each rotation of the x-ray tube, allowing full dosage radiation to be gathered from the ROI while shielding the areas outside of the ROI.

Figure 23A:
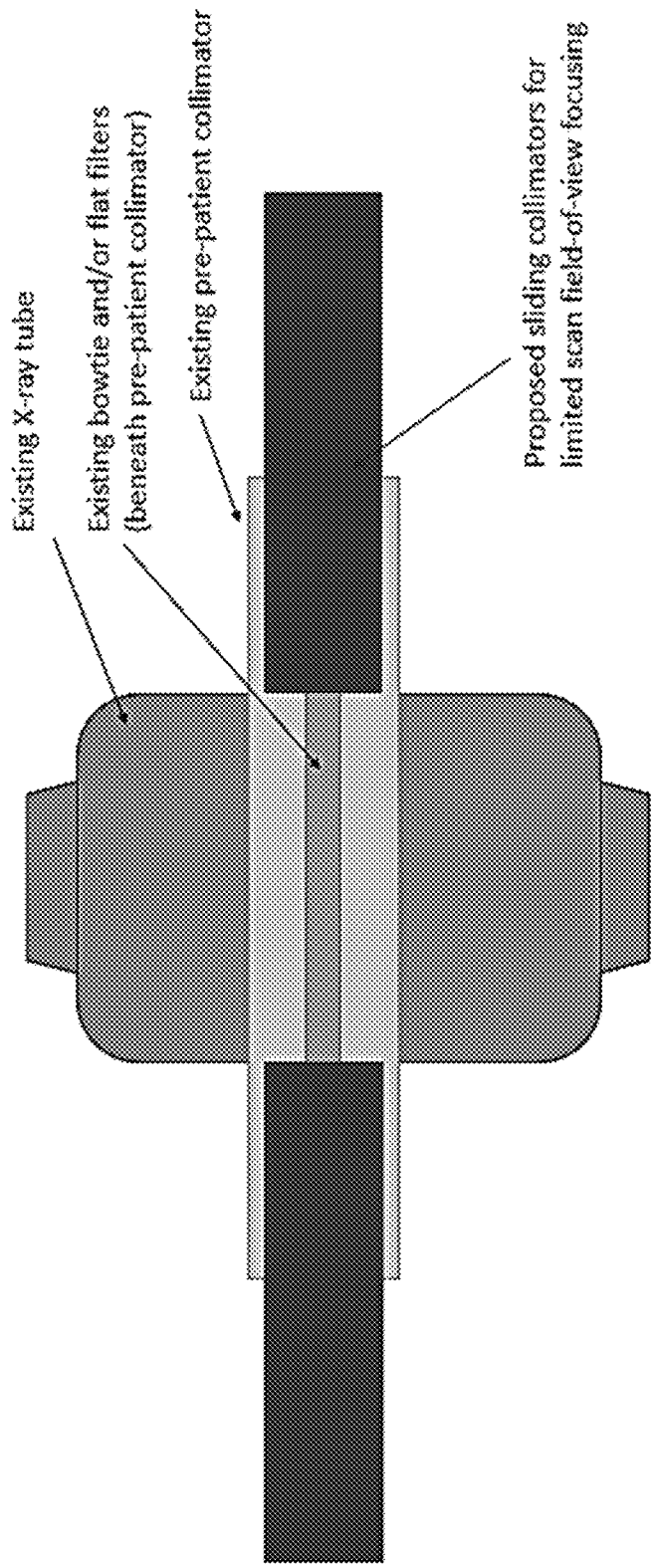
FIGS. 23A-23B are diagrams illustrating views of the sliding collimators looking up from underneath the x-ray tube/transmitter showing (A) the collimators fully open and (B) the collimators fully closed in accordance with embodiments of the present disclosure.
Figure 23B:
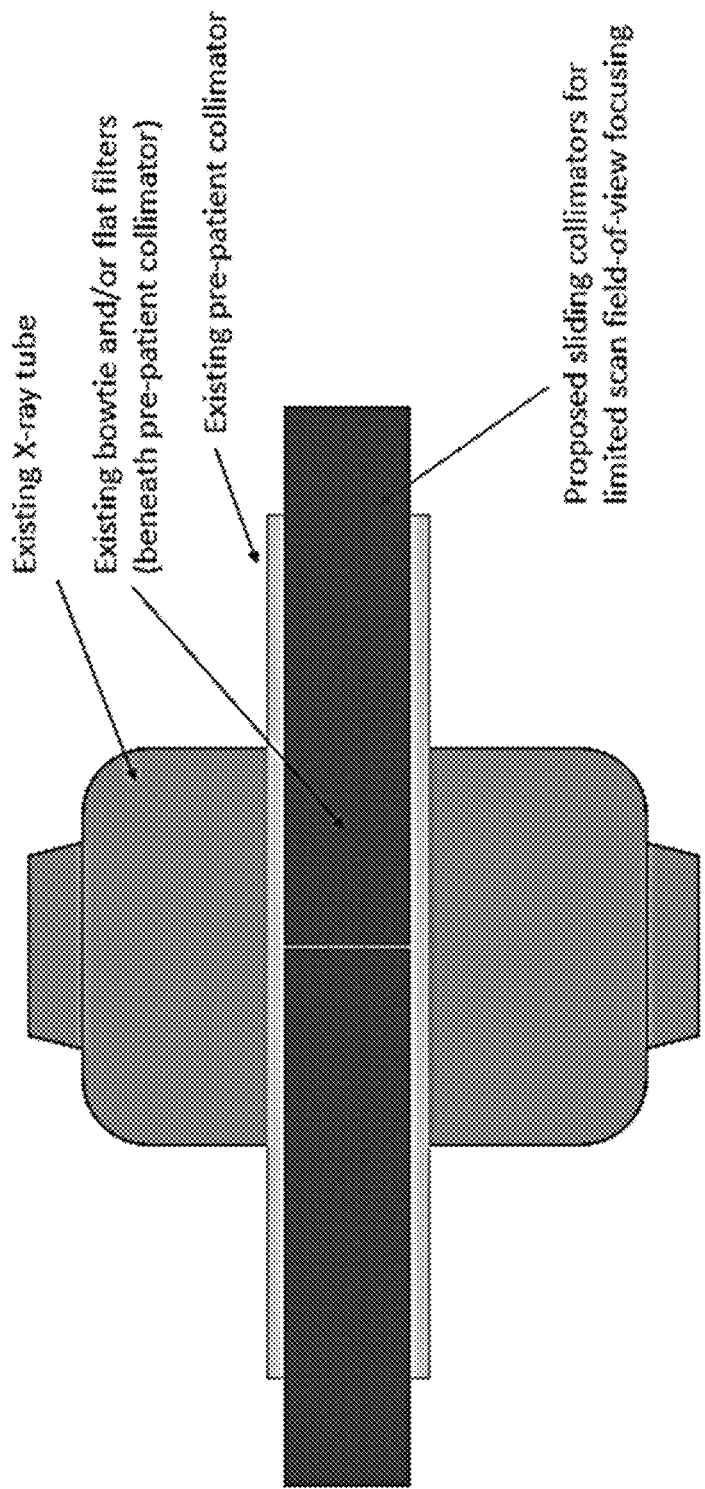

Accordingly, in one embodiment, an exemplary CT scanner of the present disclosure provides two sliding collimators at the location indicated in FIG. 22 which is between an existing pre-patient collimator and the opening of the gantry where a patient or subject would be positioned. The collimators slide back and forth using motors, to permit the opening between them to be adjustable in size from fully open (i.e., no restriction to the scan field-of-view (SFOV)) to fully closed, as shown in FIGS. 23A-23B. The collimator opening may be adjusted to any size between these extremes by a controller device coupled to the motors and/or actuators for the sliding collimators.

Figure 24A:
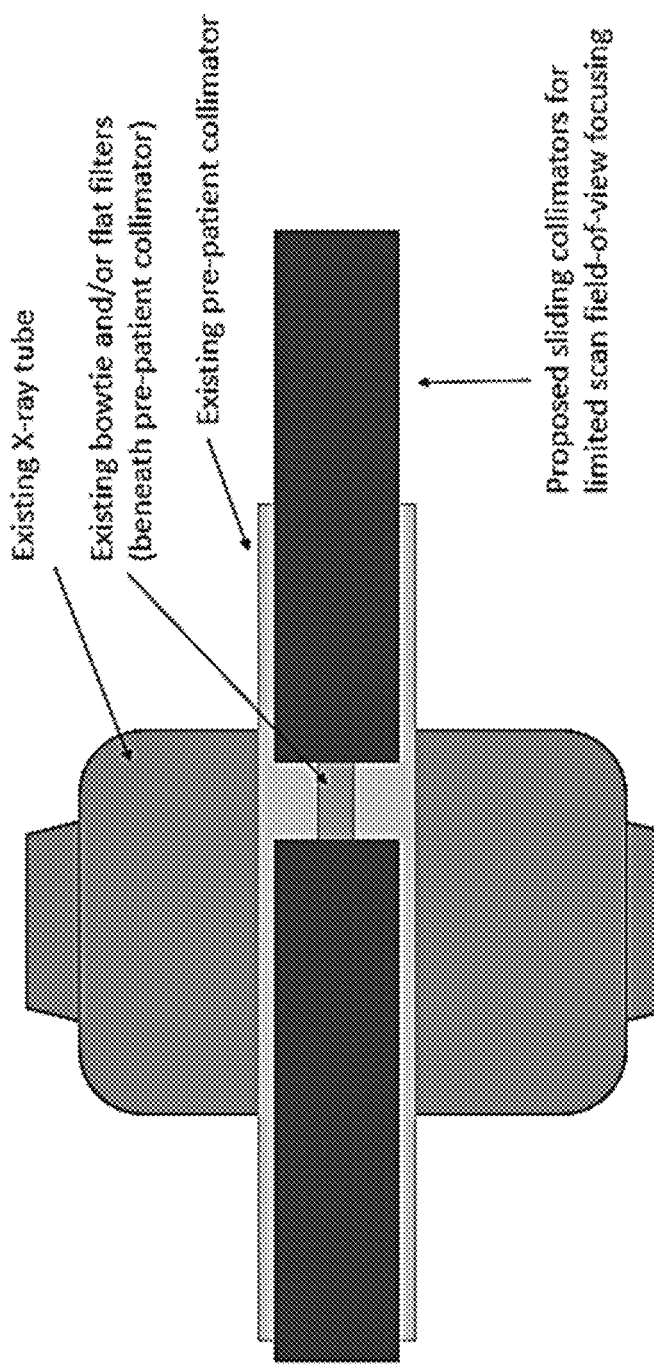
FIGS. 24A-24B are diagram illustrating views of the sliding collimators looking up from underneath the x-ray tube at two possible configurations in accordance with embodiments of the present disclosure.
Figure 24B:
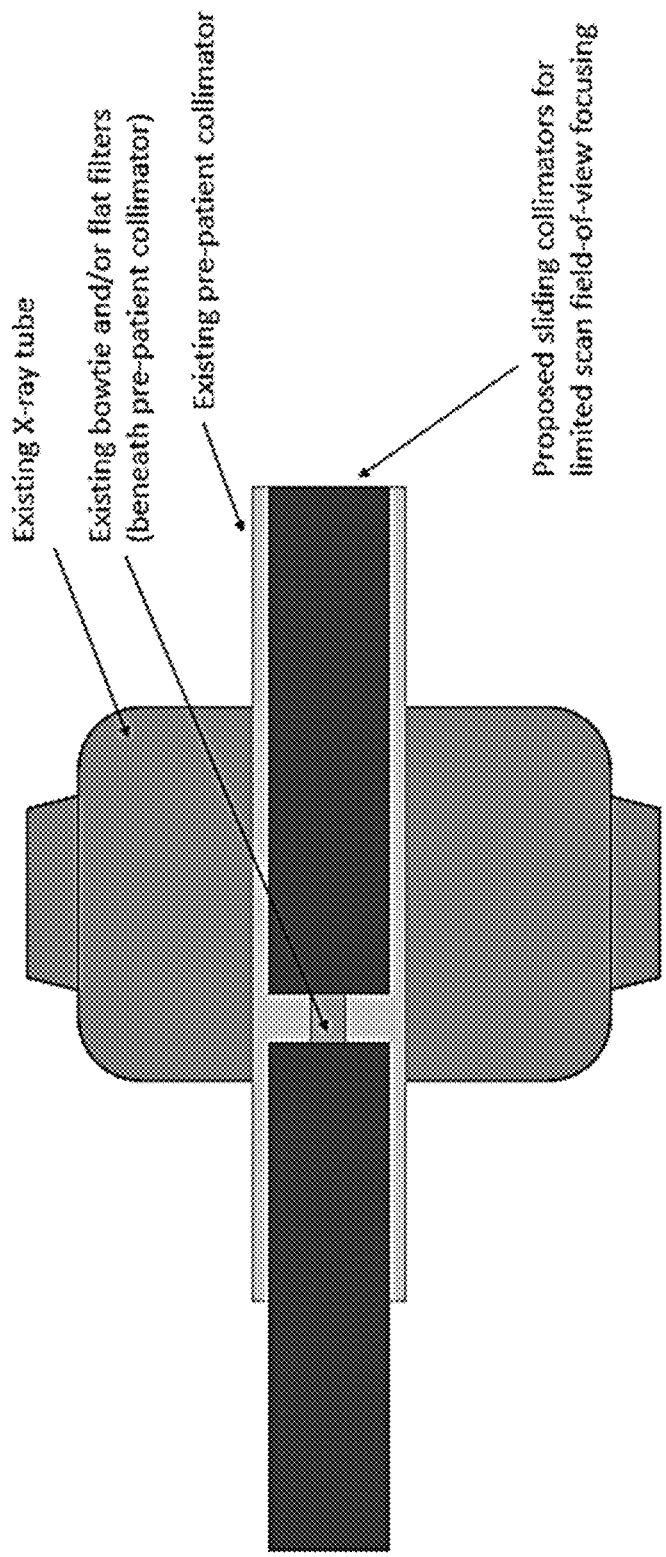
Figure 25A:
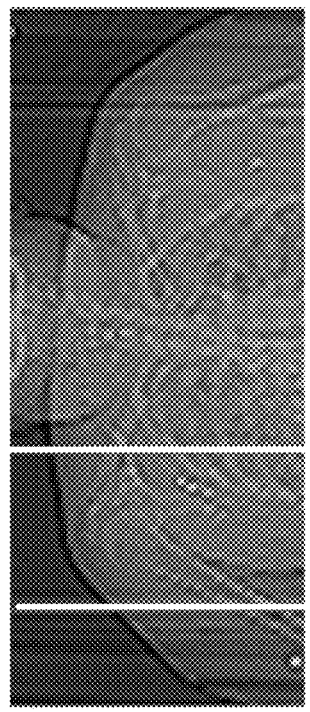
FIGS. 25A-25D are diagrams showing sample anteroposterior and lateral topograms with lines indicating the anatomy to be included in a focused CT in accordance with the present disclosure. In these examples, the exams are for (A-B) a right shoulder and (C-D) a right hip of a human subject.
Figure 25B:
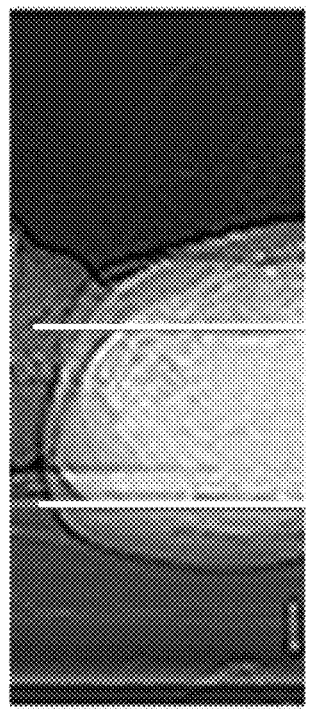
Figure 25C:
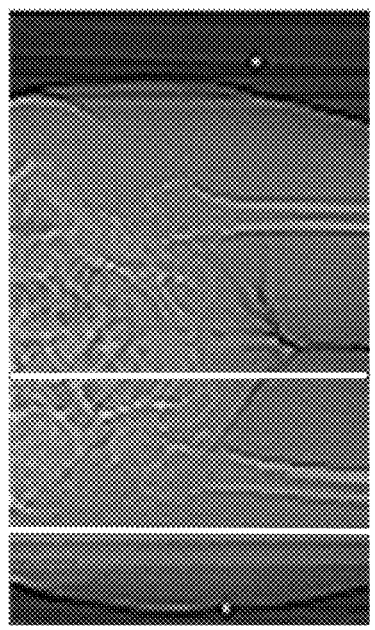
Figure 25D:
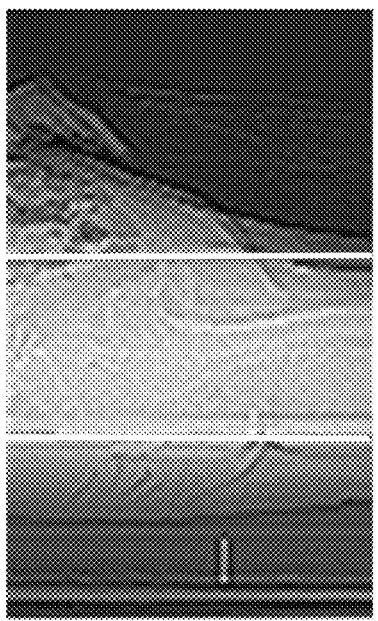
Figure 26A:
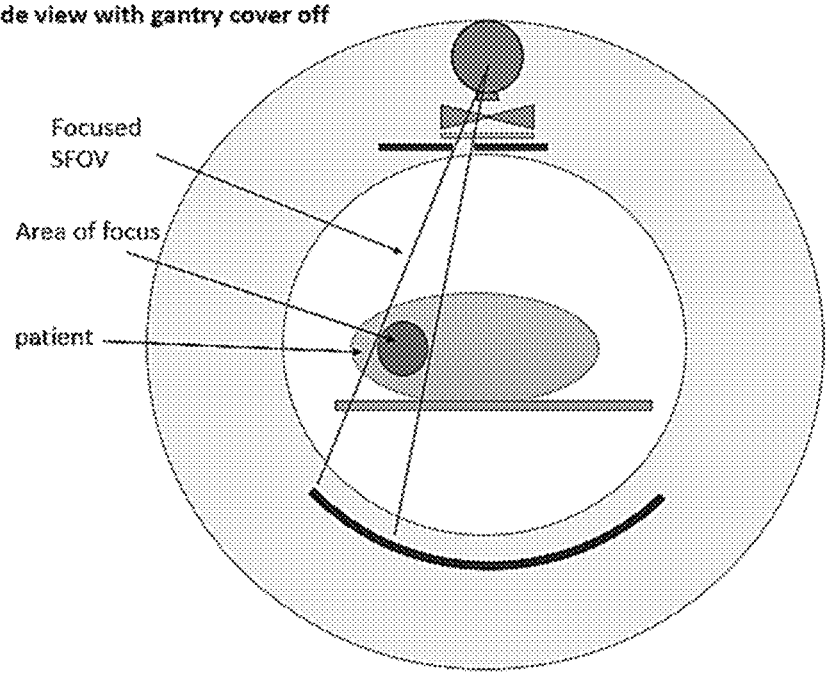
FIGS. 26A-26D are diagrams showing side views of an exemplary CT scanner showing how the sliding collimators shift the focused scan field-of-view during the rotation of the x-ray tube and detector in accordance with embodiments of the present disclosure.
Figure 26B:
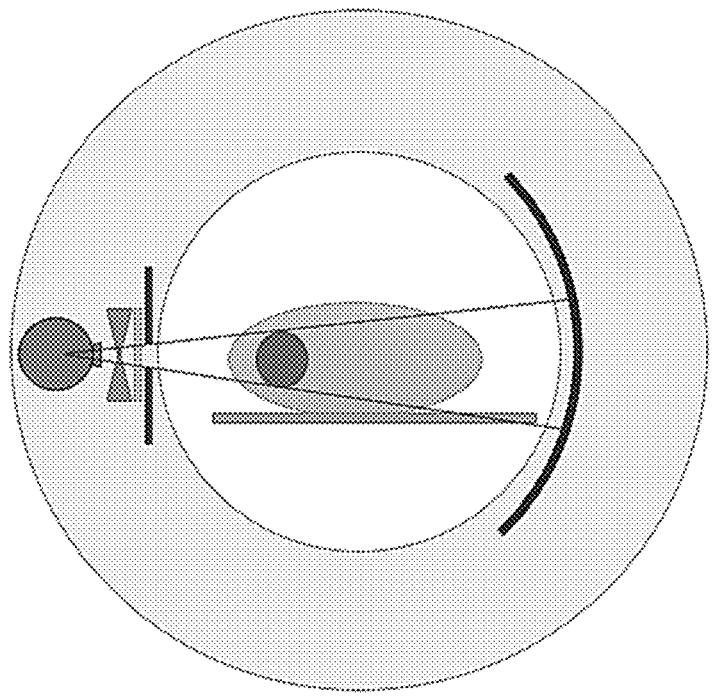
Figure 26C:
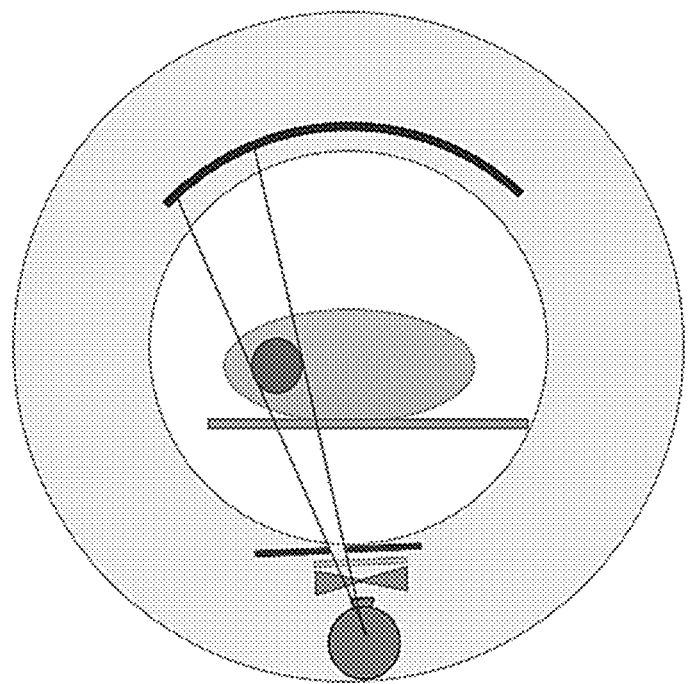
Figure 26D:
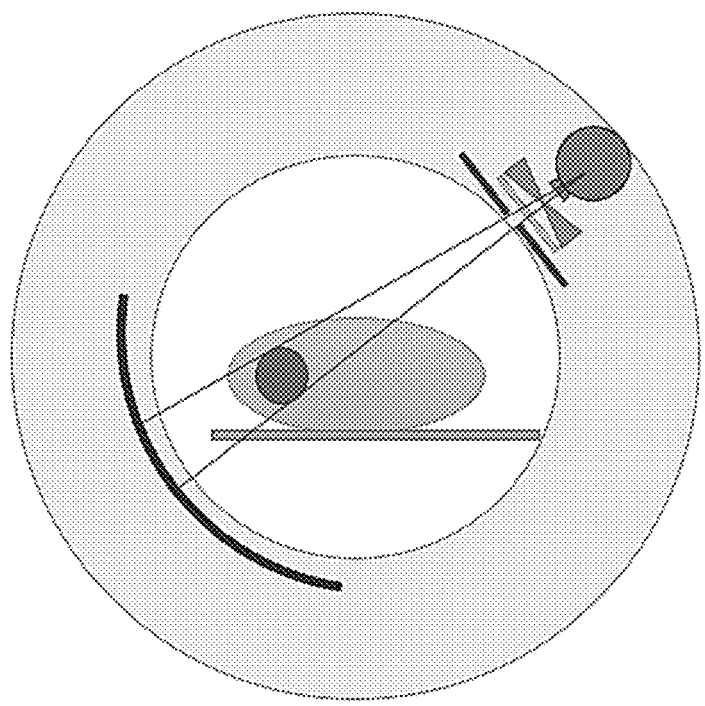

Additionally, the position of the opening may be adjustable laterally to create a focused field-of-view anywhere within the scan field-of-view, as shown in FIGS. 24A-24B. The figures show views of the sliding collimators looking up from underneath the x-ray tube. FIGS. 24A and 24B show two possible configurations of the size and position of the opening, in which the installed collimators will be able to produce an opening at any lateral position within the SFOV and with any size opening. Accordingly, the collimator movement can occur quickly enough to adjust the size and position of the opening during each rotation of the x-ray tube around the gantry.

In one embodiment, the sliding collimators are made of a material with sufficient thickness and density to reduce the measured air kerma to approximately one-tenth of the air kerma that would be measured in the beam exiting the bowtie filter and any other pre-patient filter. The exact thickness of the collimator depends on the beam quality of the CT scanner, which is dependent on manufacturer and model.

For structural integrity and the ability to adjust position quickly, the material can be a hard metal that can achieve this attenuation with a thickness of no more than a few millimeters. Appropriate materials that meet the requirements of sufficient thickness/density and structural integrity include but are not limited to copper or tungsten, in various embodiments. Approximate thicknesses would be about 6 mm of copper or 3 mm of tungsten, in various embodiments.

In one embodiment of an exemplary scanning procedure, the patient is placed on the table and positioned by the CT technologist for the CT scan. No special positioning of the patient specific to the application of a focused CT is required. The technologist acquires anteroposterior (AP) and lateral topograms. The anatomy to be included in the focused CT is marked on both topograms (in FIGS. 25A-25D) for (A-B) right shoulder and (C-D) right hip of a human subject). An exemplary CT scanner is configured to process this information to calculate the size and position of the opening in the sliding collimators in accordance with embodiments of the present disclosure.

The acquisition parameters such as kV, mA, rotation time, and pitch should be the same as those that would be used in clinical exams without the sliding collimators. No adjustment to these techniques is required. Systems using mA modulation calculated from the tomograms should continue to function correctly with the sliding collimators in place. Systems calculating mA modulation on the fly will likely need to be switched to a manual mA, in various embodiments.

In various embodiments, the sliding collimators adjust continuously or repeatedly during the CT acquisition to restrict the SFOV to the area of interest (as shown in FIGS. 26A-26D). The tissues outside the SFOV receive only the primary radiation that passes through the material of the sliding collimator, which is about 10% of the exposure within the area of interest. In FIGS. 26A-26D, four positions during CT acquisition are shown, but the collimator movement may be continuous throughout the rotation in accordance with embodiments of the present disclosure.

Functionality of an exemplary CT scanner in certain embodiments of the present disclosure or portions thereof can be implemented in hardware, software, firmware, or a combination thereof. Such software or firmware can be stored in a computer readable medium, such as memory and be executed by a suitable instruction execution system. If implemented in hardware, the hardware can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In the context of this document, a "computer-readable medium" can be any means that can contain, store, communicate, or transport a program for use by or in connection with an instruction execution system, apparatus, or device. The computer readable medium can be, for example but not limited to, an electronic, magnetic, optical, electromagnetic, infrared, or semiconductor system, apparatus, or device. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical).

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:
1. A focused tomography system comprising:
an x-ray transmitter that is configured to emit a radiation beam;
an x-ray detector that is configured to detect incident radiation from the radiation beam;
a plurality of collimators arranged between the x-ray transmitter and the x-ray detector, wherein each of the plurality of collimators are formed of a material that passes substantially 10% of incoming radiation, the plurality of collimators comprising at least an adaptive collimator;
wherein the adaptive collimator is configured to transmit the radiation beam at a first radiation dosage level when a path of the radiation beam intersects a region of interest of a subject and transmit the radiation beam at a second radiation dosage level when the path of the radiation beam does not intersect the region of interest of the subject, the second radiation dosage level being less than the first radiation dosage level and greater than 0; and
a controller connected to the focused tomography system that is configured to perform 2-D computerized tomography reconstruction of an image within the region of interest at a first image quality level for the first radiation dosage level and an image outside the region of interest at a second image quality level for the second radiation dosage level, wherein the second image quality level is lower than the first image quality level and an image of an entire slice is displayed at the first image quality level for the region of interest and the second image quality level for a region outside the region of interest.

2. The system of claim 1, wherein the adaptive collimator provides a pair of sliding collimators that actuate to adjust a size of an opening between the sliding collimators to be adjustable laterally in size, wherein the adaptive collimator is movable, via one or more motors, to position the opening at any lateral position within a scan field-of-view and to configure a size of the opening within a range from fully opened to fully closed during each rotation of the x-ray transmitter around the subject.

3. The system of claim 2, further comprising a pre-patient filter arranged between the x-ray transmitter and the adaptive collimator, wherein the pre-patient filter comprises a mechanical filter that is controllable by the controller to reduce the radiation dosage level and focus radiation from the x-ray transmitter on the region of interest.

4. The system of claim 1, wherein the adaptive collimator is formed from aluminum, copper, or tungsten material.

5. The system of claim 1, wherein the adaptive collimator comprises a pre-patient filter that focuses radiation from the x-ray transmitter on a region of interest.

6. The system of claim 1, wherein the an x-ray detector is configured to sample the radiation beam at a same rate within the region of interest and outside the region of interest.

7. The system of claim 1, wherein the adaptive collimator is configured to smoothly transition between the first radiation dosage level and the second radiation dosage level.

8. The system of claim 1, wherein the second radiation dosage level does not exceed 10% of the first radiation dosage level.

9. The system of claim 1, wherein the controller is configured to use measurements of the second radiation dosage level outside of the region of interest to determine low frequency components of an image of the region of interest.

10. A focused tomography method comprising:
arranging a plurality of collimators between an x-ray transmitter and an x-ray detector of a gantry for a computerized tomography scanner, wherein each of the plurality of collimators are formed of a material that passes substantially 10% of incoming radiation, the plurality of collimators comprising at least an adaptive collimator;

emitting a radiation beam at a first radiation dosage level when a path of the radiation beam intersects a region of interest and emitting the radiation beam at a second radiation dosage level when the path of the radiation beam does not intersect the region of interest, the second radiation dosage level being less than the first radiation dosage level and greater than 0;

detecting, via the x-ray detector, incident radiation from the radiation beam at the first radiation dosage level;

detecting, via the x-ray detector, incident radiation from the radiation beam at the second radiation dosage level;

performing 2-D computerized reconstruction, via a processor, of an image within the region of interest at a first image quality level for the first radiation dosage level and a region outside the region of interest at a second image quality level for the second radiation dosage level, wherein the second image quality level is lower than the first image quality level; and displaying an image of an entire slice at both the first image quality level for the region of interest and the second image quality level for a region outside the region of interest.

11. The method of claim 10, wherein high frequency components of the image are determined solely from the incident radiation at the first radiation dosage level whose path intersects the region of interest, wherein low frequency components of the image are determined from the incident radiation at the first radiation dosage level whose path intersects the region of interest and the incident radiation at the second radiation dosage level that does not intersect the region of interest.

12. The method of claim 10, wherein the adaptive collimator provides a pair of sliding collimators, the method further comprising:

adjusting, via a controller of the computerized tomography scanner, a size of an opening between the sliding collimators in size in order to restrict a scan field-of-view to a region of interest; and moving the adaptive collimator to position the opening at any lateral position within the scan field-of-view.

13. The method of claim 12, further comprising arranging a pre-patient filter between the x-ray transmitter and the adaptive collimator, wherein the pre-patient filter comprises a mechanical filter that is controllable by the controller to reduce the radiation dosage level and focus a radiation beam from the x-ray transmitter on the region of interest.

14. The method of claim 12, wherein the adaptive collimator comprises a pre-patient filter that focuses radiation from the x-ray transmitter on the region of interest.

15. The method of claim 12, wherein the size of the opening and/or a positioning of the opening is adjusted during each rotation of the x-ray transmitter around a subject.

16. The method of claim 10, further comprising selecting the region of interest before emitting a radiation beam.

17. The method of claim 10, further comprising sampling the radiation beam at a same rate within the region of interest and outside the region of interest.

18. The method of claim 10, further comprising smoothly transitioning between the first radiation dosage level and the second radiation dosage level.

19. The method of claim 10, wherein the second radiation dosage level does not exceed 10% of the first radiation dosage level.

* * * * *